US010430624B2

(12) United States Patent
Sundaram et al.

(10) Patent No.: US 10,430,624 B2
(45) Date of Patent: Oct. 1, 2019

(54) WIRELESS SENSOR READER ASSEMBLY

(71) Applicant: ENDOTRONIX, INC., Lisle, IL (US)

(72) Inventors: Balamurugan Sundaram, Woodridge, IL (US); Michael Nagy, Lawrenceville, GA (US); Douglas Nielsen, Chicago, IL (US); Suresh Sundaram, Dunlap, IL (US); Harry Rowland, Plainfield, IL (US)

(73) Assignee: ENDOTRONIX, INC., Lisle, IL (US)

( * ) Notice: Subject to any disclaimer, the term of this patent is extended or adjusted under 35 U.S.C. 154(b) by 0 days.

(21) Appl. No.: 15/903,809

(22) Filed: Feb. 23, 2018

(65) Prior Publication Data
US 2018/0247095 A1 Aug. 30, 2018

Related U.S. Application Data

(60) Provisional application No. 62/463,203, filed on Feb. 24, 2017.

(51) Int. Cl.
*G06K 7/10* (2006.01)
*A61B 90/98* (2016.01)
(Continued)

(52) U.S. Cl.
CPC ........ *G06K 7/10425* (2013.01); *A61B 5/0031* (2013.01); *A61B 5/0215* (2013.01);
(Continued)

(58) Field of Classification Search
CPC .................................................. G06K 7/10425
(Continued)

(56) References Cited

U.S. PATENT DOCUMENTS 3,714,595 A 1/1973 Denenberg
3,872,455 A 3/1975 Fuller
(Continued)

FOREIGN PATENT DOCUMENTS

EP 2612595 7/2013
HK 1147906 8/2011
(Continued)

OTHER PUBLICATIONS

International Searching Authority, European Patent Office; International Search Report and Written Opinion for International Application No. PCT/US2018/019475; dated May 22, 2018.
(Continued)

*Primary Examiner* — Santiago Garcia
(74) *Attorney, Agent, or Firm* — McDonald Hopkins LLC

(57) ABSTRACT

Disclosed are a reader device, system, and method for communicating with a wireless sensor. The reader device may be configured to analyze the strength of a response signal transmitted from the wireless sensor in response to an excitation pulse generated by the reader device. In one embodiment, the reader device may be configured to engage be placed in a plurality of modes to allow the reader to transmit a signal, such as a short pulse of energy or a short burst of radio frequency energy to cause the wireless sensor to output a resonant signal. The reader device may receive the resonant signal from the wireless sensor and evaluate it against predetermined values. The evaluated signals may be used to assess the strength and the proximity of the reader device relative to the wireless sensor as it is implanted in a patient.

56 Claims, 11 Drawing Sheets

(51) Int. Cl.
  *A61B 5/00* (2006.01)
  *A61B 5/0215* (2006.01)
  *H04Q 9/00* (2006.01)
  *G16H 10/65* (2018.01)
  *A61B 5/0402* (2006.01)

(52) U.S. Cl.
  CPC .......... *A61B 90/98* (2016.02); *G06K 7/10386* (2013.01); *H04Q 9/00* (2013.01); *A61B 5/0402* (2013.01); *A61F 2250/0002* (2013.01); *B81B 2201/02* (2013.01); *B81B 2201/06* (2013.01); *G16H 10/65* (2018.01); *H04Q 2209/00* (2013.01); *H04Q 2209/47* (2013.01); *H04Q 2209/50* (2013.01); *H04Q 2209/86* (2013.01)

(58) Field of Classification Search
  USPC ...................................................... 340/10.3
  See application file for complete search history.

(56) References Cited

U.S. PATENT DOCUMENTS

| | | |
|---|---|---|
| 3,888,708 A | 6/1975 | Wise |
| 3,943,915 A | 3/1976 | Severson |
| 3,958,558 A | 5/1976 | Dunphy |
| 4,023,562 A | 5/1977 | Hynecek |
| 4,026,276 A | 5/1977 | Chubbuck |
| 4,037,324 A | 7/1977 | Andreasen |
| 4,067,235 A | 1/1978 | Markland |
| 4,127,110 A | 11/1978 | Bullara |
| 4,206,762 A | 6/1980 | Cosman |
| 4,385,636 A | 5/1983 | Cosman |
| 4,407,296 A | 10/1983 | Anderson |
| 4,485,813 A | 12/1984 | Anderson |
| 4,511,858 A | 4/1985 | Charavit |
| 4,531,244 A | 7/1985 | Hamas |
| 4,531,526 A | 7/1985 | Genest |
| 4,567,459 A | 1/1986 | Folger |
| 4,644,420 A | 2/1987 | Buchan |
| 4,651,089 A | 3/1987 | Haigh |
| 4,701,826 A | 10/1987 | Mikkor |
| 4,730,496 A | 3/1988 | Knecht |
| 4,815,472 A | 3/1989 | Wise |
| 4,881,410 A | 11/1989 | Wise |
| 4,953,387 A | 9/1990 | Johnson |
| 4,966,034 A | 10/1990 | Bock |
| 5,005,577 A | 4/1991 | Frenkel |
| 5,006,819 A | 4/1991 | Buchan |
| 5,013,396 A | 5/1991 | Wise |
| 5,046,497 A | 9/1991 | Millar |
| 5,055,838 A | 10/1991 | Wise |
| 5,059,543 A | 10/1991 | Wise |
| 5,108,420 A | 4/1992 | Marks |
| 5,113,868 A | 5/1992 | Wise |
| 5,227,798 A | 7/1993 | Hildebrand |
| 5,257,630 A | 11/1993 | Broitman |
| 5,262,127 A | 11/1993 | Wise |
| 5,282,827 A | 2/1994 | Kensey |
| 5,296,255 A | 3/1994 | Gland |
| 5,334,952 A | 8/1994 | Maddy |
| 5,343,064 A | 8/1994 | Spangler |
| 5,377,524 A | 1/1995 | Wise |
| 5,417,235 A | 5/1995 | Wise |
| 5,522,267 A | 6/1996 | Lewis |
| 5,564,434 A | 10/1996 | Halperin |
| 5,581,248 A | 12/1996 | Spillman |
| 5,690,674 A | 11/1997 | Diaz |
| 5,872,520 A | 2/1999 | Seifert |
| 5,920,233 A | 7/1999 | Denny |
| 5,992,769 A | 11/1999 | Wise |
| 6,015,386 A | 1/2000 | Kensey |
| 6,024,704 A | 2/2000 | Meador |
| 6,025,725 A | 2/2000 | Gershenfeld |
| 6,053,873 A | 4/2000 | Govari |
| 6,109,113 A | 8/2000 | Chavan |
| 6,111,520 A | 8/2000 | Allen |
| 6,126,675 A | 10/2000 | Shchervinsky |
| 6,140,144 A | 10/2000 | Najafi |
| 6,150,681 A | 11/2000 | Allen |
| 6,171,252 B1 | 1/2001 | Roberts |
| 6,174,322 B1 | 1/2001 | Schneidt |
| 6,190,400 B1 | 2/2001 | Van De Moer |
| 6,206,835 B1 | 3/2001 | Spillman |
| 6,232,150 B1 | 5/2001 | Lin |
| 6,278,379 B1 | 8/2001 | Allen |
| 6,287,256 B1 | 9/2001 | Park |
| 6,309,350 B1 | 10/2001 | VanTassel |
| 6,312,380 B1 | 11/2001 | Hoek |
| 6,331,163 B1 | 12/2001 | Kaplan |
| 6,338,284 B1 | 1/2002 | Najafi |
| 6,359,444 B1 | 3/2002 | Grimes |
| 6,378,360 B1 | 4/2002 | Bartels |
| 6,416,474 B1 | 7/2002 | Penner |
| 6,432,737 B1 | 8/2002 | Webster |
| 6,441,503 B1 | 8/2002 | Webster |
| 6,442,413 B1 | 8/2002 | Silver |
| 6,447,449 B1 | 9/2002 | Fleischman |
| 6,454,720 B1 | 9/2002 | Clerc |
| 6,459,253 B1 | 10/2002 | Krusell |
| 6,471,656 B1 | 10/2002 | Shalman |
| 6,477,901 B1 | 11/2002 | Tadigadapa |
| 6,499,354 B1 | 12/2002 | Najafi |
| 6,505,516 B1 | 1/2003 | Frick |
| 6,517,481 B2 | 2/2003 | Hoek |
| 6,532,834 B1 | 3/2003 | Pinto |
| 6,535,116 B1 | 3/2003 | Zhou |
| 6,570,457 B2 | 5/2003 | Fischer |
| 6,579,235 B1 | 6/2003 | Abita |
| 6,592,608 B2 | 7/2003 | Fisher |
| 6,636,769 B2 | 10/2003 | Govari |
| 6,645,143 B2 | 11/2003 | VanTassel |
| 6,647,778 B2 | 11/2003 | Sparks |
| 6,658,300 B2 | 12/2003 | Govari |
| 6,662,663 B2 | 12/2003 | Chen |
| 6,666,826 B2 | 12/2003 | Salo |
| 6,667,725 B1 | 12/2003 | Simons |
| 6,680,654 B2 | 1/2004 | Fischer |
| 6,682,490 B2 | 1/2004 | Roy |
| 6,713,828 B1 | 3/2004 | Chavan |
| 6,749,568 B2 | 6/2004 | Fleischman |
| 6,749,622 B2 | 6/2004 | McGuckin |
| 6,757,566 B2 | 6/2004 | Weiner |
| 6,764,446 B2 | 7/2004 | Wolinsky |
| 6,779,406 B1 | 8/2004 | Kuznia |
| 6,783,499 B2 | 8/2004 | Schwartz |
| 6,789,429 B2 | 9/2004 | Pinto |
| 6,805,667 B2 | 10/2004 | Christopherson |
| 6,824,521 B2 | 11/2004 | Rich |
| 6,838,640 B2 | 1/2005 | Wise |
| 6,840,956 B1 | 1/2005 | Wolinsky |
| 6,844,213 B2 | 1/2005 | Sparks |
| 6,855,115 B2 | 2/2005 | Fonseca |
| 6,890,300 B2 | 5/2005 | Lloyd |
| 6,893,885 B2 | 5/2005 | Lemmerhirt |
| 6,916,310 B2 | 7/2005 | Sommerich |
| 6,923,625 B2 | 8/2005 | Sparks |
| 6,926,670 B2 | 8/2005 | Rich |
| 6,932,114 B2 | 8/2005 | Sparks |
| 6,935,010 B2 | 8/2005 | Tadigadapa |
| 6,939,299 B1 | 9/2005 | Petersen |
| 6,945,939 B2 | 9/2005 | Turcott |
| 6,959,608 B2 | 11/2005 | Bly |
| 6,968,743 B2 | 11/2005 | Rich |
| 6,981,958 B1 | 1/2006 | Gharib |
| 6,994,666 B2 | 2/2006 | Shannon |
| 6,994,672 B2 | 2/2006 | Fleischman |
| 7,001,398 B2 | 2/2006 | Carley |
| 7,004,015 B2 | 2/2006 | Chang-Chien |
| 7,004,034 B2 | 2/2006 | Chen |
| 7,013,734 B2 | 3/2006 | Zdeblick |
| 7,018,337 B2 | 3/2006 | Hood |
| 7,025,727 B2 | 4/2006 | Brockway |
| 7,025,778 B2 | 4/2006 | Hayashi |
| 7,028,550 B2 | 4/2006 | Zdeblick |

(56) References Cited

U.S. PATENT DOCUMENTS

| | | |
|---|---|---|
| 7,046,964 B1 | 5/2006 | Sullivan |
| 7,048,756 B2 | 5/2006 | Eggers |
| 7,059,176 B2 | 6/2006 | Sparks |
| 7,059,195 B1 | 6/2006 | Liu |
| 7,059,196 B1 | 6/2006 | Liu |
| 7,066,031 B2 | 6/2006 | Zdeblick |
| 7,073,387 B2 | 7/2006 | Zdeblick |
| 7,081,125 B2 | 7/2006 | Edwards |
| 7,131,945 B2 | 11/2006 | Fink |
| 7,134,341 B2 | 11/2006 | Gimionsky |
| 7,137,953 B2 | 11/2006 | Eigler |
| 7,146,861 B1 | 12/2006 | Cook |
| 7,147,604 B1 | 12/2006 | Allen |
| 7,149,587 B2 | 12/2006 | Wardle |
| 7,162,926 B1 | 1/2007 | Guziak |
| 7,169,106 B2 | 1/2007 | Fleischman |
| 7,181,975 B1 | 2/2007 | Bradley |
| 7,190,937 B1 | 3/2007 | Sullivan |
| 7,192,001 B2 | 3/2007 | Wise |
| 7,198,603 B2 | 4/2007 | Penner |
| 7,211,048 B1 | 5/2007 | Najafi |
| 7,219,021 B2 | 5/2007 | Liu |
| 7,228,735 B2 | 6/2007 | Sparks |
| 7,245,117 B1 | 7/2007 | Joy |
| 7,252,006 B2 | 8/2007 | Tai |
| 7,252,010 B2 | 8/2007 | Ohta |
| 7,261,733 B1 | 8/2007 | Brown |
| 7,273,457 B2 | 9/2007 | Penner |
| 7,284,442 B2 | 10/2007 | Fleischman |
| 7,290,454 B2 | 11/2007 | Liu |
| 7,347,822 B2 | 3/2008 | Brockway |
| 7,347,826 B1 | 3/2008 | Karicherla |
| 7,425,200 B2 | 9/2008 | Brockway |
| 7,432,723 B2 | 10/2008 | Ellis |
| 7,466,120 B2 | 12/2008 | Miller |
| 7,483,805 B2 | 1/2009 | Sparks |
| 7,498,799 B2 | 3/2009 | Allen |
| 7,519,325 B2 | 4/2009 | Wakim |
| 7,550,978 B2 | 6/2009 | Joy |
| 7,566,308 B2 | 7/2009 | Stahmann |
| 7,641,619 B2 | 1/2010 | Penner |
| 7,647,831 B2 | 1/2010 | Corcoran |
| 7,666,151 B2 | 2/2010 | Sullivan |
| 7,679,355 B2 | 3/2010 | Allen |
| 7,686,762 B1 | 3/2010 | Najafi |
| 7,686,768 B2 | 3/2010 | Bodecker |
| 7,839,153 B2 | 11/2010 | Joy |
| 7,936,174 B2 | 5/2011 | Ellis |
| 8,154,389 B2 * | 4/2012 | Rowland ............... A61B 5/0031 340/13.2 |
| 8,271,093 B2 | 9/2012 | Von Arx |
| 8,360,984 B2 | 1/2013 | Yadav |
| 8,384,524 B2 * | 2/2013 | Cobianu ............ G06K 19/0672 235/375 |
| 8,432,265 B2 | 4/2013 | Rowland |
| 8,493,187 B2 * | 7/2013 | Rowland ............... A61B 5/0031 340/10.1 |
| 8,570,186 B2 * | 10/2013 | Nagy .................... A61B 5/0031 340/870.02 |
| 8,852,099 B2 | 10/2014 | Von Arx |
| 8,866,788 B1 | 10/2014 | Birnbaum |
| 9,044,150 B2 | 6/2015 | Brumback |
| 9,089,717 B2 | 7/2015 | Forsell |
| 9,305,456 B2 | 4/2016 | Rowland |
| 9,489,831 B2 | 11/2016 | Nagy |
| 9,721,463 B2 | 8/2017 | Rowland |
| 9,723,997 B1 | 8/2017 | Lamego |
| 9,867,552 B2 | 1/2018 | Rowland |
| 9,894,425 B2 | 2/2018 | Nagy |
| 2002/0045921 A1 | 4/2002 | Wolinsky |
| 2002/0072656 A1 | 6/2002 | Vantassel |
| 2002/0115920 A1 | 8/2002 | Rich |
| 2002/0138009 A1 | 9/2002 | Brockway |
| 2002/0151816 A1 | 10/2002 | Rich |
| 2002/0177782 A1 | 11/2002 | Penner |
| 2002/0188207 A1 | 12/2002 | Richter |
| 2003/0062957 A1 | 4/2003 | Terashima |
| 2003/0136417 A1 | 7/2003 | Fonseca |
| 2003/0139677 A1 | 7/2003 | Fonseca |
| 2003/0139771 A1 | 7/2003 | Fisher |
| 2003/0158584 A1 | 8/2003 | Cates |
| 2003/0191496 A1 | 10/2003 | Edwards |
| 2004/0102806 A1 | 5/2004 | Broome |
| 2004/0158138 A1 | 8/2004 | Kilcoyne |
| 2004/0220637 A1 | 11/2004 | Zdeblick |
| 2004/0239504 A1 | 12/2004 | Kalinin |
| 2004/0255643 A1 | 12/2004 | Wise |
| 2004/0260164 A1 | 12/2004 | Kilcoyne |
| 2005/0013685 A1 | 1/2005 | Ricketts |
| 2005/0015014 A1 | 1/2005 | Fonseca |
| 2005/0025322 A1 | 2/2005 | Henson |
| 2005/0043601 A1 | 2/2005 | Kilcoyne |
| 2005/0049634 A1 | 3/2005 | Chopra |
| 2005/0080346 A1 | 4/2005 | Gianchandani |
| 2005/0090719 A1 | 4/2005 | Scheiner |
| 2005/0103114 A1 | 5/2005 | Bly |
| 2005/0145187 A1 | 7/2005 | Gray |
| 2005/0154321 A1 | 7/2005 | Wolinsky |
| 2005/0160825 A1 | 7/2005 | Zdeblick |
| 2005/0160827 A1 | 7/2005 | Zdeblick |
| 2005/0187482 A1 | 8/2005 | O'Brien |
| 2005/0201178 A1 | 9/2005 | Ho |
| 2005/0228308 A1 | 10/2005 | Iddan |
| 2005/0287287 A1 | 12/2005 | Parker |
| 2005/0288596 A1 | 12/2005 | Eigler |
| 2005/0288604 A1 | 12/2005 | Eigler |
| 2005/0288722 A1 | 12/2005 | Eigler |
| 2006/0047205 A1 | 3/2006 | Ludomirsky |
| 2006/0052821 A1 | 3/2006 | Abbott |
| 2006/0064133 A1 | 3/2006 | Von Arx |
| 2006/0064134 A1 | 3/2006 | Mazar |
| 2006/0064142 A1 | 3/2006 | Chavan |
| 2006/0064143 A1 | 3/2006 | Von Arx |
| 2006/0085039 A1 | 4/2006 | Hastings |
| 2006/0107749 A1 | 5/2006 | Liu |
| 2006/0116590 A1 | 6/2006 | Fayram |
| 2006/0117859 A1 | 6/2006 | Liu |
| 2006/0122522 A1 | 6/2006 | Chavan |
| 2006/0129050 A1 | 6/2006 | Martinson |
| 2006/0144155 A1 | 7/2006 | Liu |
| 2006/0161171 A1 | 7/2006 | Schwartz |
| 2006/0177956 A1 | 8/2006 | O'Brien |
| 2006/0178583 A1 | 8/2006 | Montegrande |
| 2006/0178695 A1 | 8/2006 | Decant |
| 2006/0196277 A1 | 9/2006 | Allen |
| 2006/0206146 A1 | 9/2006 | Tenerz |
| 2006/0212047 A1 | 9/2006 | Abbott |
| 2006/0217762 A1 | 9/2006 | Maahs |
| 2006/0217763 A1 | 9/2006 | Abbott |
| 2006/0217764 A1 | 9/2006 | Abbott |
| 2006/0219022 A1 | 10/2006 | Ohta |
| 2006/0229488 A1 | 10/2006 | Ayre |
| 2006/0241354 A1 | 10/2006 | Allen |
| 2006/0244465 A1 | 11/2006 | Kroh |
| 2006/0247724 A1 | 11/2006 | Gerber |
| 2006/0271078 A1 | 11/2006 | Modesitt |
| 2006/0287602 A1 | 12/2006 | O'Brien |
| 2006/0287700 A1 | 12/2006 | White |
| 2007/0007240 A1 | 1/2007 | Wise |
| 2007/0028698 A1 | 2/2007 | Guziak |
| 2007/0032734 A1 | 2/2007 | Najafi |
| 2007/0049980 A1 | 3/2007 | Zielinski |
| 2007/0049984 A1 | 3/2007 | Osypka |
| 2007/0060959 A1 | 3/2007 | Salo |
| 2007/0061089 A1 | 3/2007 | Liu |
| 2007/0073351 A1 | 3/2007 | Zielinski |
| 2007/0074579 A1 | 4/2007 | Cook |
| 2007/0088388 A1 | 4/2007 | Opolski |
| 2007/0096715 A1 | 5/2007 | Joy |
| 2007/0100215 A1 | 5/2007 | Powers |
| 2007/0106246 A1 | 5/2007 | Modesitt |
| 2007/0106328 A1 | 5/2007 | Wardle |
| 2007/0106333 A1 | 5/2007 | Fernandez |
| 2007/0112358 A1 | 5/2007 | Abbott |

(56) References Cited

U.S. PATENT DOCUMENTS

| | | |
|---|---|---|
| 2007/0118039 A1 | 5/2007 | Bodecker |
| 2007/0142727 A1 | 6/2007 | Zhang |
| 2007/0149880 A1 | 6/2007 | Willis |
| 2007/0157734 A1 | 7/2007 | Skwara |
| 2007/0160748 A1 | 7/2007 | Schugt |
| 2007/0191717 A1 | 8/2007 | Rosen |
| 2007/0197957 A1 | 8/2007 | Hunter |
| 2007/0210786 A1 | 9/2007 | Allen |
| 2007/0261497 A1 | 11/2007 | O'Brien |
| 2007/0274565 A1 | 11/2007 | Penner |
| 2007/0282210 A1 | 12/2007 | Stern |
| 2008/0015421 A1 | 1/2008 | Penner |
| 2008/0033527 A1 | 2/2008 | Nunez |
| 2008/0058632 A1 | 3/2008 | Tai |
| 2008/0082005 A1 | 4/2008 | Stern |
| 2008/0281212 A1 | 11/2008 | Nunez |
| 2009/0115396 A1 | 5/2009 | Allen |
| 2009/0224773 A1 | 9/2009 | Joy |
| 2009/0224837 A1 | 9/2009 | Joy |
| 2010/0026318 A1 | 2/2010 | Kroh |
| 2010/0039234 A1* | 2/2010 | Soliven .............. H04B 5/02 340/10.1 |
| 2010/0161004 A1 | 6/2010 | Najafi |
| 2010/0294937 A1* | 11/2010 | Finch .............. G08B 13/04 250/340 |
| 2012/0296234 A1 | 11/2012 | Wilhelm |
| 2013/0331036 A1 | 12/2013 | Baker |
| 2014/0257058 A1* | 9/2014 | Clarysse .............. G06Q 50/22 600/301 |
| 2014/0306807 A1* | 10/2014 | Rowland .............. H04Q 9/00 340/10.3 |
| 2017/0023542 A1* | 1/2017 | Wang .............. G01N 33/487 |
| 2017/0061168 A1* | 3/2017 | Sundaram .............. G06K 7/0095 |

FOREIGN PATENT DOCUMENTS

| | | |
|---|---|---|
| JP | 2007210547 | 8/2007 |
| WO | WO/2005/107583 | 11/2005 |
| WO | WO2006096582 | 9/2006 |
| WO | WO/2006/130488 | 12/2006 |
| WO | WO2010042055 | 4/2010 |
| WO | WO2010117356 | 10/2010 |
| WO | WO2012149008 | 11/2012 |
| WO | WO2013184283 | 12/2013 |
| WO | WO2017025300 | 2/2017 |

OTHER PUBLICATIONS

The International bureau of WIPO, International Search Report and Written Opinion of the International Searching Authority, dated Aug. 25, 2010, International App. No. PCT/US10/27951, Applicant Endotronix, Inc.

The International Bureau of WIPO, International Search Report and Written Opinion of International Searching Authority, dated Aug. 4, 2008, International Application No. PCT/US08/03475.

International Search Authority, The International Search Report and The Written Opinion, dated Jun. 30, 2009, International Application No. PCT/US2009/039730.

Extended European Search Report, Endotronix, Inc., Application No. 10762085.8-2319/2417590, dated Jan. 4, 2013.

International Preliminary Report on Patentability, Endotronix, Inc., PCT/US2012/034979, dated Nov. 7, 2013.

International Search Report and the Written Opinion of the International Searching Authority, Endotronix, Inc., PCT/US2012/34979, dated Nov. 2, 2012.

International Search Report, dated Nov. 14, 2008, for corresponding PCT patent application No. PCT/US2008/069217 filed Jul. 3, 2008 (4 pages).

Nagumo, J., Uchiyama, A. Kimoto, S., Watanuki, T., Hori, M., Suma, K., Ouchi, A., Kumano, M., and Watanabe, H., Echo Capsule for Medical Use (A Batteryless Endoradiosonde), IRE Transaction on Bio-Medical Electronics, pp. 195-199, 1962.

Haynes, H.E. & Witchey, A.L, Medical Electronics; The Pill That "Talks" DEP, 1960, pp. 52-54, Cambden, NJ.

Collins, Carter, Miniature Passive Pressure Transensor for Implanting in the Eye, Transactions on Bio-Medical Engineering, vol. BME-14, No. 2, pp. 74-83, Apr. 1967.

European Patent Office, Extended European Search Report, Application No. 17000257.0, dated Jun. 14, 2017.

\* cited by examiner

WIRELESS SENSOR READER ASSEMBLY

CROSS-REFERENCE TO RELATED APPLICATIONS

This application claims priority to U.S. Provisional Patent App. No. 62/463,203 entitled "WIRELESS SENSOR READER ASSEMBLY" and filed on Feb. 24, 2017, which is hereby incorporated by reference in its entirety.

TECHNICAL FIELD

This invention relates generally to a system for communicating with wireless sensors, and more particularly to improving the functionality of a reader device and system for communicating with wireless sensors.

BACKGROUND

Wireless sensor systems that employ resonant circuit technology are known. These systems may utilize a passive wireless sensor in remote communication with excitation and reader circuitry. Often the wireless sensor is implanted at a specific location, such as within the human body, to detect and report a sensed parameter. In some systems, the sensed parameter varies the resonant frequency of the wireless sensor. A reader device may detect the resonant frequency of the wireless sensor to determine the sensed parameter.

Wireless sensor systems may generally include a reader unit or device that may be configured to be placed in a use condition for taking readings from the sensor and in a resting condition in which it is not communicating with the sensor. For example, a reader unit may be handheld or battery operated and be adapted for use a few minutes each day. This reader unit may also be configured to sit on a recharging ("docking") station during times of non-use. Sensor/reader systems may incorporate many types of wireless technology: active & passive sensors, continuous wave (CW) & modulated data transmission, and analog & digital type systems.

In one application, passive wireless sensor systems may employ resonant circuit technology. Passive wireless sensor systems may be pressure monitoring devices for use by themselves or incorporated into other medical devices including, without limitation, pacemakers, defibrillators, drug elution devices, or ventricular assist devices (VADs). In one embodiment, a medical device includes one or more sensors that are configured to be positioned at a desired location within the human body. The sensor may be fabricated using microelectromechanical systems (MEMS) technology and may be configured to transmit wireless data to an external receiver/reader to facilitate transmission of diagnostic health data to a physician, clinician, a nurse, a patient's caregiver, or the patient.

One such sensor formed using a MEMS technique has an inductive and capacitive nature. The sensor comprises an inductor (L) and a capacitor (C) connected together in parallel, commonly called an LC tank circuit. The geometry of the sensor allows for the deformation of a capacitive plate with increased pressure. This deformation leads to a deflection of the plate and hence a change in the capacitance value of the system. The LC tank circuit also generates an electronic resonating frequency. This resonating frequency is related to the inductive and capacitance values of the circuit and will change with the deflection of capacitor plates under changing pressure. This emitted resonating frequency signal is received by an external wireless receiver/reader and deciphered into a correlative pressure reading.

Such sensors may also include wireless data transmission capability. The device may require no battery or internal power. Rather, the sensor may be powered by an inductively coupled electromagnetic (EM) field that is directed towards its inductor coil. The receiver/reader device may provide the electromagnetic field by generating a radio frequency (RF) burst or other signal. The inductor receives energy from the EM field to cause the sensor LC tank to resonate and store energy. When the external EM field is removed, the inductance and capacitance form a parallel resonant circuit to radiate energy through the inductor which acts as an antenna. This oscillating circuit will then produce RF signals, whose frequency is proportional to the capacitive value of the sensor, which varies with pressure. The inductor coil may serve both as an inductor creating the oscillating RF signals having a frequency proportional to the capacitance of the sensor at a certain pressure, and as an antenna coil emitting the RF signal generated by the LC tank circuitry.

In one embodiment, the pressure sensor may include an inductor/capacitor circuitry assembled in a parallel configuration. In other embodiments, it may include a piezoelectric, piezo-resistive or capacitive pressure sensor. In the inductor/capacitor circuitry, the resonant frequency of the energized circuit will change with the internal pressure of the patient. The sensor transmits sensed or detected pressure readings wirelessly to an external system receiver through RF signals without the requirements of an internal powering system. In a particular embodiment, the sensor may be energized through electromagnetic fields that are directed to a circuitry of the sensor.

Current designs for wireless sensor readers and related systems, such as those disclosed in commonly owned U.S. Pat. No. 8,154,389 filed on Apr. 7, 2009, U.S. Pat. No. 8,432,265 filed on Mar. 19, 2012, U.S. Pat. No. 8,493,187 filed on Mar. 19, 2010, and U.S. Pat. No. 8,570,186 filed on Apr. 25, 2012, U.S. Pat. No. 9,867,552 filed on Jun. 29, 2012, U.S. Pat. No. 9,305,456 filed on Apr. 9, 2013, U.S. Pat. No. 9,489,831 filed on Sep. 30, 2013, U.S. Pat. No. 9,721,463 filed on Mar. 29, 2016, U.S. Pat. No. 9,894,425 filed on Nov. 7, 2016 are incorporated by reference herein. These patents disclose systems configured to communicate wirelessly with a sensor at a remote location and obtain a reading.

Wireless sensor readers intended for frequent use by medical patients at home are particularly useful for taking measurements of internal body parameters of interest to caregivers. In order to ensure patient compliance in taking these readings, consistently, and correctly, however, there is a need for improving the functionality of this system and in particular improving the functionality and usability of the reader. Further, there is a need to allow a user to easily incorporate the reader and associated system within their day to day lifestyle and for improving the reliability of the reader in the field, to ensure functionality, accuracy, and secure data management.

BRIEF DESCRIPTION OF THE DRAWINGS

Objects and advantages together with the operation of the invention may be better understood by reference to the following detailed description taken in connection with the following illustrations, wherein.

SUMMARY

Figure 1:
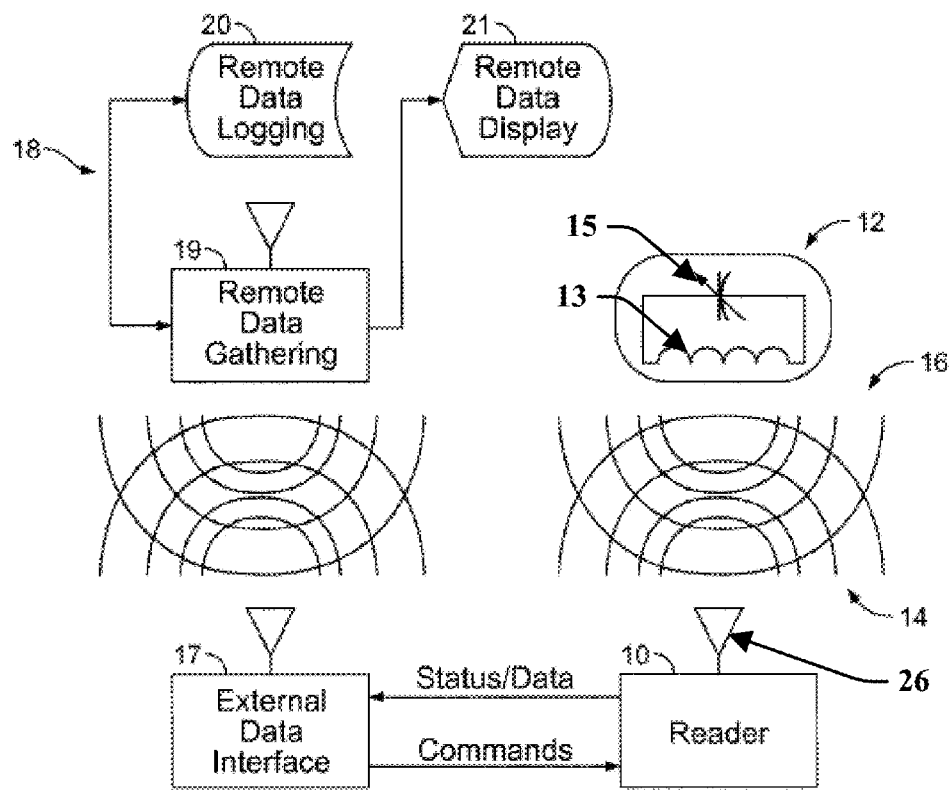
FIG. 1 illustrates a block diagram of a prior art passive wireless sensor and reader system.

Disclosed are a reader device, system, and method for communicating with a wireless sensor. The reader device may be configured to analyze the strength of a response signal transmitted from the wireless sensor in response to an excitation pulse generated by the reader device. In one embodiment, the reader device may be configured to be placed in a plurality of modes to allow the reader to transmit a signal, such as a short pulse of energy or a short burst of radio frequency energy to cause the wireless sensor to output a resonant ring signal. The reader device may receive the response signal from the wireless sensor and evaluate at least one of its characteristics, for example signal strength, against predetermined values. The evaluated signals may be used to assess the proximity of the reader device relative to the wireless sensor as it is implanted in a patient.

In one embodiment, provided is a system for wirelessly sensing a parameter from a remote location. The system includes a handheld reader device configured to communicate with a wireless sensor wherein said reader device includes a plurality of modes to establish communication with said wireless sensor, said modes comprising: A docked mode wherein said handheld reader device is not in use. A search mode wherein said handheld reader device attempts to establish the proper distance acceptable for taking readings from the wireless sensor, and a read mode wherein said handheld reader device reads and samples response signals from the wireless sensor. Said wireless sensor may be configured to change its resonant frequency in proportion to at least one sensed parameter and may be a passive sensor. A remote data interface may communicate with said handheld reader device.

A docking station may be configured to receive said handheld reader device and to electrically communicate with said handheld reader device. The reader device may include a battery and the docking station may be configured to recharge said battery of the reader device. The docking station may include a remote data interface that is configured to accept raw frequency data and format it for communication with a remote device. The docking station may be configured to provide a data link function and a data storage function. When said handheld reader device is in said search mode, said handheld reader device may be configured to receive a plurality of signals from said wireless sensor and compare the strength of said signals received from said wireless sensor to a predetermined threshold value. The comparison of said signals to said predetermined threshold value may be made by a system external to said reader device, may be displayed on a screen, and may be used to provide feedback to the user of said handheld reader device. Said feedback may include audible, visual, or haptic signals and may be configured to guide said user to locate said handheld reader device in a position aligned with said sensor for wireless communication. Said feedback may be configured to inform said user that alignment with said sensor has been achieved establishing a locked condition between the handheld reader device and the wireless sensor and causing said handheld reader device to enter said read mode.

Said handheld reader device may process the feedback to determine that a sufficient number of acceptable reading samples are obtained during read mode. Said handheld reader device may be configured to determine that a reading attempt of the wireless sensor is successful or unsuccessful and to provide an audible, visual, or haptic signal to the user identifying a passed or a failed reading attempt.

The handheld reader device may enter said search mode automatically upon being removed from said docking station. The handheld reader device may be configured to enter a travel mode, wherein said travel mode places said handheld reader device in a state conducive to transport to a new location such that said handheld reader device is configured to inhibit all audible, visual, and haptic signals. A user may place said handheld reader device into said travel mode by a switch, said switch comprises at least one of: a mechanical switch, a capacitive switch, an accelerometer, a tilt sensor, a spoken command, and a fingerprint sensor. The handheld reader device and said docking station may be configured to execute a self-test while the reader device is in dock mode.

In another embodiment, provided is a method for communicating between a handheld reader device and a wireless sensor. Here a reader device configured to communicate with a wireless sensor may be provided. Said reader device may be placed in close proximity to said wireless sensor. A plurality of excitation pulses may be generated from an antenna of said reader device to excite the wireless sensor to generate at least one response signal. Said reader device may receive at least one response signal from said wireless sensor. The at least one response signal may be compared with a threshold measurement. The reader device and said wireless sensor may be determined to be in a locked condition for further communication.

The wireless sensor may change its resonant frequency in proportion to at least one sensed parameter. The reader device may be placed in a docked mode by connecting said reader device to a docking station. The docking station may charge a battery of said reader device. The reader device may provide an audible, visual, or haptic signal to guide a user to position said reader device relative to said sensor. The reader device may provide an audible, visual, or haptic signal to guide a user through a search mode and a read mode.

In another embodiment, provided is a wireless sensor reader device comprising a transmit circuit configured to generate an excitation pulse to cause a wireless sensor to emit a response signal. An antenna may be configured to transmit said excitation pulse and receive said response signal. A lock circuit may be provided for evaluating if the wireless sensor is in sufficient proximity to the reader device to take readings from said wireless sensor. The reader device may be handheld. The reader device may further include a fingerprint sensor. The reader device may be configured to ensure that designated users operate said reader device. The reader device may be configured to associate data from a fingerprint sensor with the data captured during a reading event. The reader device may further comprise a circuit for measuring electrocardiogram data wherein said circuit comprises remote electrodes that connect to said reader device. The electrocardiogram circuit may include electrodes that are built into the surface of said reader device. The circuit for measuring electrocardiogram data may be selected from among the following types of electrocardiogram measurement: one lead, two leads, four leads, eight leads, and twelve leads. The reader device may measure and record data from said wireless sensor and said electrocardiogram simultaneously.

The reader device may further include a tilt sensor. Said tilt sensor may be an accelerometer wherein said tilt sensor is configured to record an orientation of said reader device with respect to gravity. The accelerometer may be configured to record motion of the reader device during a reading mode. An audible, visual, or haptic signal may be provided to prompt a user to enter data representative of at least one of a user's name, a spoken response, and to associate said spoken response with data derived from a given reading. The electrocardiogram data may be combined with a parametric data from said wireless sensor to enable hemodynamic analysis. The reader device may include circuitry for determining its geographic location.

The reader device may upload said response signal data to a remote database and processor. The response signal data may be uploaded as raw data and processed according to an algorithm to produce processed data. The remote database and processor may store said raw data and said processed data. The algorithm may utilize a manufacturer's calibration data originally obtained during the manufacture of said reader device or said wireless sensor. The algorithm may utilize calibration data obtained during surgical implantation of said wireless sensor into a patient. The algorithm may utilize historical data processed by said reader device. The algorithm may be a learning algorithm. The processed data may be representative of strength of said response signal received by said wireless sensor. The reader device may be configured to reject said response signals that fail to meet said at least one predetermined threshold. The algorithm may utilize data taken from a second sensor configured to measure a parameter different from the one measured by the first said wireless sensor. The second sensor may be selected from one of: barometer, accelerometer, tilt sensor, blood glucose sensor, inspiration spirometer, pulse oximeter, arterial blood pressure sensor, electrocardiogram, weight scale, or echo-cardiogram. The algorithm may utilize data taken from said patient's medical record or the algorithm may utilize data taken from said patient's answers to health related questions. The second sensor may be connected to said reader device. The algorithm may be a hemodynamic algorithm.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the present invention.

Figure 2:
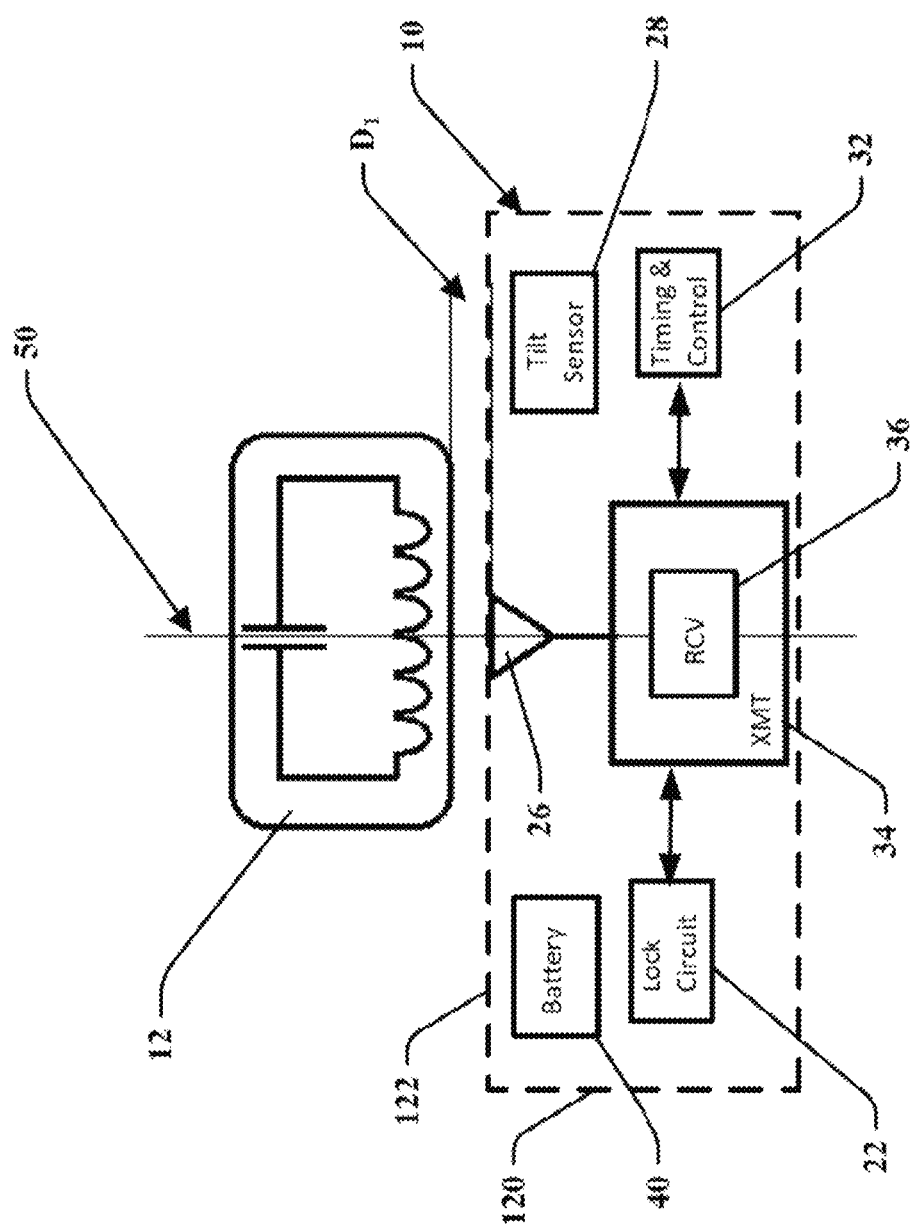
FIG. 2 illustrates an embodiment of the reader device and wireless sensor system.

A device, system, and method for communicating a wireless sensor with a reader device are disclosed. As illustrated by FIGS. 1 and 2, a reader device 10 may be configured to remotely and wirelessly communicate with a sensor 12. The sensor 12 may be wireless and may be a passive type sensor. To initiate communication, the reader device 10 may be placed in proximity to the sensor 12 and capable of exciting the sensor 12 by transmitting a signal 14 (excitation pulse), such as a radio frequency ("RF") pulse, at or near the resonant frequency of the sensor 12. Note that as used herein, "excitation" pulse is any signal 14 transmitted from the reader to the sensor, that evinces a response signal 12 from the sensor. For passive sensors with no internal energy storage, the excitation signal 14 may power the sensor 12, enabling it to emit a response signal 16. For active sensors with internal storage, the excitation pulse may be a data signal only. As used herein, "excitation", "stimulus" or "stimulating signal' are used interchangeably. An "energizing" signal is a subset of excitation signal that transfers power to the sensor. After the excitation pulse 14 is extinguished, the sensor 12 may emit a response signal 16 for a short period of time in response to the signal/excitation pulse 14 from the reader device 10. In particular, the sensor 12 may be designed to be placed within the cardiovascular system of a human to provide a signal that may be a function of a sensed parameter (such as blood pressure) that is desirable to be identified. The reader device 10 may be configured to receive and ascertain the frequency of the response signal 16 via wireless communication with the sensor 12 and extrapolate the sensed parameter. In another embodiment, the excitation signal 14 may be a continuous signal that is not extinguished prior to receiving response signal 16. In this embodiment, excitation signal 14 and response signal 16 may continue simultaneously, and may be set at different frequencies to avoid mutual interference.

The sensor 12 may also be an active sensor, powered by a battery, which does not require a power pulse to be transmitted from the reader device 10, but may respond to a data stimulus or excitation signal 14 from reader device 10. The sensor 12 may also communicate via a digital or analog wireless signal using any of the many modulation schemes well-known in the art. The term "battery" as used herein refers to any type of electrochemical energy storage device. A "battery" may have one or more cells, and may be a primary (non-rechargeable) or secondary (rechargeable) type.

As illustrated by FIG. 1, the reader device 10 may also communicate with a data interface 17. The reader device 10 and data interface 17 may be connected wirelessly, and may be physically distant from one another. The reader device 10 may send information, such as data related to the sensor 12 to the data interface 17. The reader device 10 may further send information regarding the status of the reader device 10 to the data interface 17. The data interface 17 may provide configuration information to the reader device 10. For example, the data interface 17 may provide information regarding schedules and intervals for sampling the sensor 12.

The data interface 17 may communicate with a remote data gathering system 18 to exchange status and control signals, as well as provide sensor data. The remote data system 18 may include a data gathering module 19 to receive data from the data interface 17, a data logging module 20 to store the received data, and a data display 21 to display the sensor data. In one embodiment, the reader 10 may upload raw frequency data obtained from sensor 12 to data interface 17. Data interface 17 may in turn upload the raw data to data gathering system 18, which uses stored calibration coefficients and preset algorithms to process the raw frequency data and convert it to the parameter of interest. Data gathering system 18 may further use identification data from the reader 10 or sensor 12 to associate the processed data with a given user, based on a pre-loaded associative database. In an embodiment, data interface 17 may be a device that accepts raw frequency data and formats it for uploading via TCPIP to the internet. Further, data gathering system 18 may reside on a remote server on the internet, and may make its processed, associated data available to authorized users, such as clinicians responsible for care of the patient taking the data at home. The data transfers in this embodiment may occur in real time or after initial raw data acquisition by the reader 10.

This disclosure may apply to any embodiment of a wireless sensor system that is configured to communicate with a reader device, e.g., a reader device 10 configured to supply a stimulus signal 14 and subsequently receive a response signal such as a ring signal 16 from a wireless sensor implanted in the body. In some embodiments, stimulus signal 14 may be an energizing signal that transfers power to a passive sensor. However, various reader and sensor type systems (e.g. active sensors, passive sensors, continuous wave sensors, modulated sensors, analog sensors and digital type systems) may be utilized in the system described by this disclosure.

Figure 3:
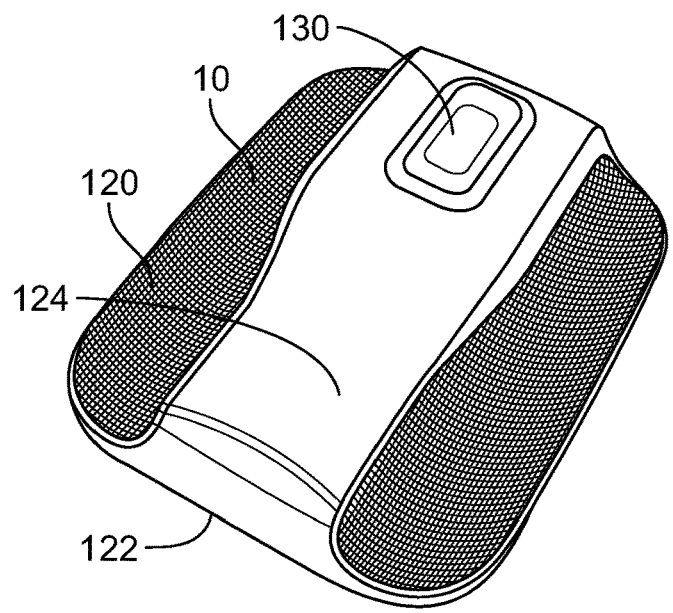
FIG. 3 illustrates an embodiment of the reader device.
Figure 4:
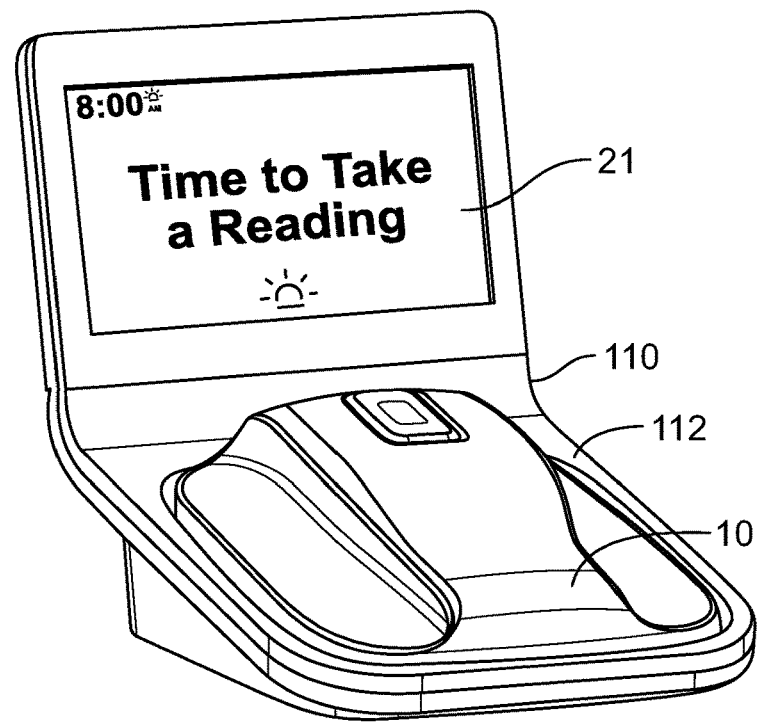
FIG. 4 illustrates an embodiment of a docking station with the reader device.

FIG. 3 illustrates an embodiment of the reader device 10 and FIG. 4 illustrates the reader device 10 and associated docking station 110. The reader device 10 may be a portable handheld device that may be carried by the user or placed in a port 112 of the docking station 110. The docking station 110 may be kept in a convenient location for the user such as the user's home or office. The reader device 10 may be associated with the docking station 110 to charge and communicate with the reader device 10. The data interface 17 may be located within the docking station 110. Likewise, the remote data gathering system 18 may communicate with the docking station 110 to exchange status and control signals, as well as receive sensor data. The docking station 110 may include the remote data system 18, the data gathering module 19, the data logging module 20, and the data display 21. Alternatively, any one of these modules may be separate from the docking station 110 and may be remotely located such as on a networked or dedicated standalone server device.

The reader device 10 may include a housing 120 having an ergonomic design including a reader surface 122 and a handle portion 124. The reader surface 122 may be the active surface at which the reader's antenna 26 is located. The reader surface 122 may be opposite from the handle portion 124 to allow a user or third party to grasp and manipulate the reader device 10 with one hand and to position the reader surface 122 in proximity to the sensor 12 as it may be located within a patient. In one embodiment, the reader device 10 may weigh between about 0.5 kg (1.1 lbs.) to about 2 kg (4.4 lbs.) and more particularly weigh between about 0.5 kg (1.1 lbs.) to about 1.25 kg (2.76 lbs.) and may weigh about 0.75 kg (1.65 lbs.). The housing 120 of the reader device 10 may include various electrical components therein. The housing 120 may be opened to allow a user to access these components, such as for maintenance or replacement purposes. In particular, the housing 120 may be opened with the use of a tool unique to the housing 120. This tool may be specialized or include an uncommon shape to increase secure access, allow minimal access therein, and prevent unauthorized access to the housed components. In one embodiment, the reader device 10 may weigh between about 0.1 kg to about 1 kg, allowing typical medical patients to hold the reader 10 against the body with one hand, and thus take readings by themselves, without assistance.

The reader device 10 may include the antenna 26 positioned adjacent to the reader surface 122 for transmitting the excitation pulse 14 from the surface 122. The reader device 10 may include a timing and control circuitry 32 to configure and activate the other circuits in the reader device 10. The timing and control circuitry 32 may include control interfaces operated by digital or low-frequency signals. The timing and control circuitry 32 may generate an RF signal that is sent to a transmit circuitry. The transmit circuitry 34 may receive the RF signal and send out the stimulus pulse 14 during a search mode and a read mode to excite the sensor 12 as will be discussed more fully below.

The antenna 26 may be connected to the transmit circuitry 34 and a receive circuitry 36. The transmit circuitry 34 may utilize the antenna 26 for transmitting the stimulus pulse 14, while the receive circuitry 36 may utilize the antenna 26 for receiving the response signal 16. In an embodiment, the antenna 26 may be connected to both the transmit circuitry 34 and the receive circuitry 36 at all times instead of being switched between transmit and receive. This shared antenna 26 design may have isolation features to prevent damage to the receive circuitry. Specifically, the voltage at the antenna 26 may exceed 200 volts peak-to-peak during transmission of the excitation pulse 14, and may be single-digit millivolts, decaying rapidly to micro-volts, during reception immediately following the response signal 16 from the sensor 12. The transmit circuitry 34 and receive circuitry 36 may be located within the reader device 10.

While the reader device 10 is described as having a shared antenna 26, it will be appreciated that the reader device 10 may incorporate more than one antenna to separately perform the functions of transmitting the stimulus pulse 14 and receiving the response signal 16.

The reader device 10 may further include a phase locked loop (PLL) to receive and lock onto the response signal 16, which may be a ring signal in an embodiment. The receive circuitry 36 may amplify and condition the ring signal 16 before sending it to the PLL. The PLL may include a voltage controlled oscillator ("VCO") that is configured to change as necessary to match the frequency and phase of the ring signal 16. The VCO interfaces with a frequency counter which counts the VCO frequency, and provides the count to an external interface circuitry for transfer to the data interface 17 as raw frequency data.

Each component of the reader device 10 may be designed to operate efficiently and reduce power consumption. The transmit circuitry 34 of the reader device 10 may be configured to transmit the stimulus pulse 14 to the sensor 12 by way of the antenna 26. The excitation pulse 14 may be a fixed or rapidly varying frequency burst at or near the resonant frequency of the sensor 12. For example, the excitation pulse 14 may be a fixed frequency burst within several bandwidths of the sensor 12 resonant frequency. Alternatively, the excitation pulse 14 may be a fixed or rapidly varying frequency burst or sweep of a very short duration at or near a frequency harmonically related to the sensor 12 resonant frequency. The excitation pulse 14 may be dithered between two or more frequency values. The excitation pulse 14 may also be an ultra-wide band pulse. This plurality of excitation pulse 14 approaches may be effective because the response signal 16 may be received when the excitation pulse 14 transmissions have ceased. Therefore, excitation pulse 14 transmissions may be limited to frequency bands, amplitudes, and modulation schemes acceptable to regulatory government bodies. Radio frequency regulations generally may not apply to the sensor 12 as the sensor 12 may be a purely passive device.

For embodiments where the sensor is a passive resonant type, the stimulus or excitation pulse 14 may not require significant transmission time because a single short transmission of energy may be sufficient to stimulate a sufficiently strong sample of the ring signal 16. Reader 10 power consumption may be reduced by using a lower transmission duty cycle, thereby reducing the duty cycle of transmit, receive, counting, and digital processing circuitry. By reducing power consumption, battery power becomes a much more viable option to power the system as a rechargeable battery 40 may also be within the reader device 10.

The excitation pulse 14 may be configured to maximize several system parameters. For example, if a fixed frequency excitation pulse 14 is used, the frequency of the burst may be configured to maximize parameters such as maximum allowable transmit peak power, maximum freedom from in-band or near-band interference during the "receive" interval while the PLL is being locked to the ring signal 16, maximum worldwide acceptance of a particular frequency for reader transmissions for the desired sensor purpose, or other such criteria. To utilize a fixed frequency in this manner, the frequency of the excitation pulse 14 may be predetermined before the sensor 12 is to be sampled. This allows the excitation pulse 14 to be focused towards the resonant frequency of the sensor 12 in which the excitation pulse 14 is not a swept frequency. Use of a fixed frequency allows power consumption to be reduced.

Once the excitation pulse 14 is transmitted by the transmit circuitry at a fixed frequency, the receive circuitry may be configured to acquire the ring signal 16. Voltages at the antenna 26 may reach upwards of 200 volts peak-to-peak during transmission of the excitation pulse, requiring only approximately 60 pico-farads of capacitance to tune the antenna 26. In an embodiment, a 1 pico-farad capacitor may be used as a high impedance input current limiting device on a 13.5 MHz transmit circuit.

As illustrated by FIGS. 3 and 4, one or more input members 130 such buttons, touch surfaces, roller balls, sliders, or other tactile controls may be located along the housing 120 to allow the user to activate various functions of the reader device 10. The input member 130 may also include a finger print reader that allows a user to securely use a reader associated with only the designated patient or sensor. The input member 130 may be programmed to receive a user's fingerprint to access use of the reader device 10 or to prevent the unauthorized use of the reader device 10. The input member 130 may be programmed to allow various users and to restrict access to various functions. The reader device 10 may also include an individual ID number associated with each reader device 10. The ID number may be categorized and associated with any measured and communicated data to allow the data to be matched with the correct user. Further, any data that is collected by the reader device 10 may also include a time stamp identifying the date and time that that data was collected or processed. Further, the reader 10 may include GPS or similar location finding functionality, allowing location to be recorded with each sensor reading.

Other methods for ensuring correct user identification with date associated with a reader device 10 may also be provided. For example, the reader device 10 may use a voice audio cue that asks the user his/her name just before or after a reading session. The reader device 10 may receive and record the response and identify if access is granted or rejected for use of the reader and/or access to the data. The recorded sound file may be associated with the data from that session.

Secure or positive user identification built into the reader device 10 may be advantageous when the sensor 12 is attached to the user, for example, if the sensor 12 is implanted inside the user's body, or if the sensor 12 does not include self-identification capability or otherwise include secured communication.

The reader device 10 may be battery powered and placed in the docking station 110 to be charged as shown in FIG. 4. The docking station 110 may be plugged into a standard wall socket and provide power to recharge the battery of the reader device 10. The reader device 10 and docking station 110 may be easily transportable by the user and may provide a wireless and secure link to a network for remote communication. Alternatively, the reader device 10 may include a port for a wired connection to the docking station or other external device to allow for battery charge or data transmission. The reader device 10 and its docking station 110 may be configurable to enter a travel mode, in which the devices remain quiet and in a dark mode.

Figure 5:
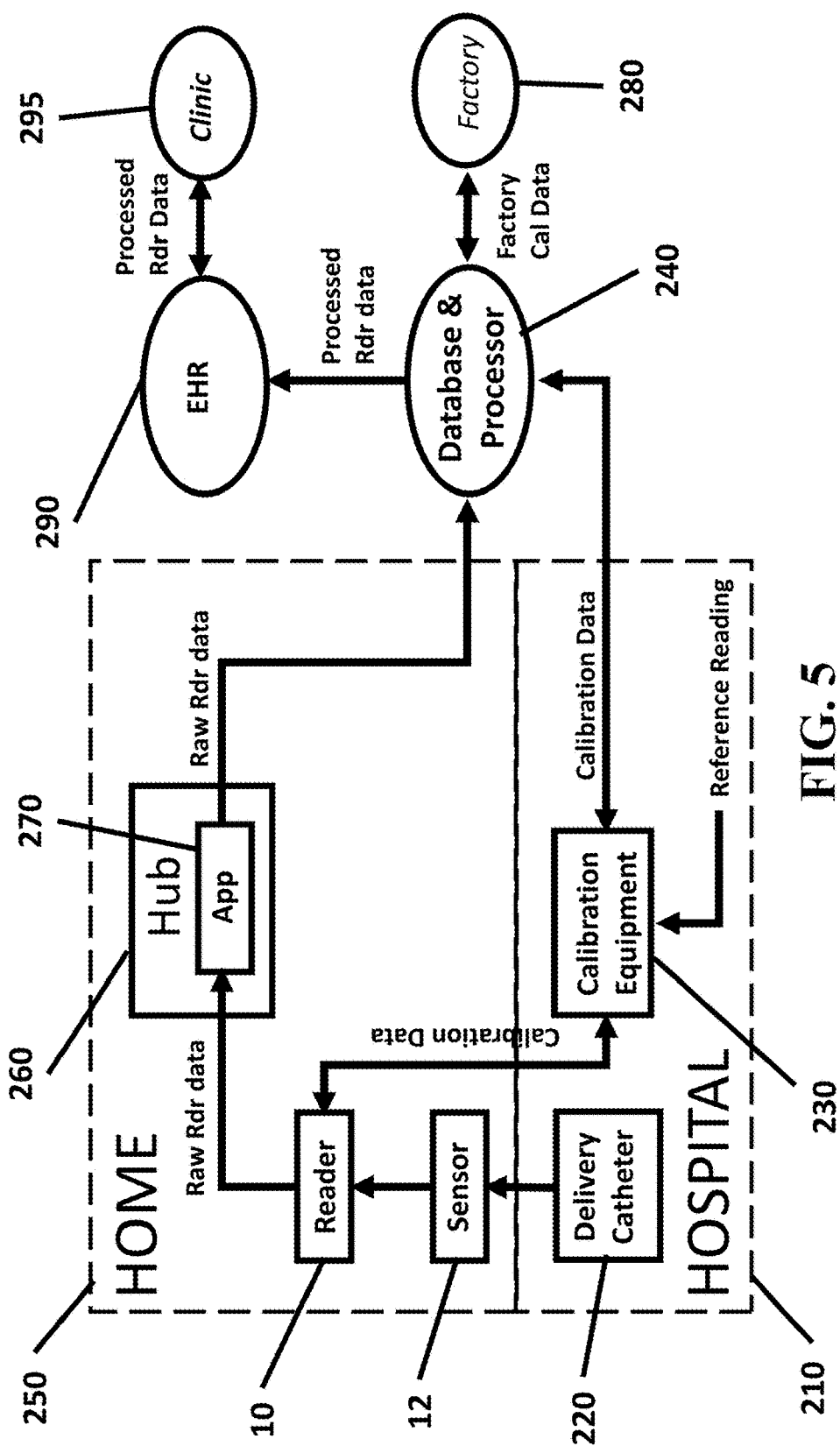
FIG. 5 illustrates a block diagram of a wireless sensor and reader system according to the present disclosure.

In one embodiment, the reader device 10 may be part of a larger system of devices, which work together to measure a parameter from inside a medical patient's body, and communicate the results of the measurement to medical personnel at a clinic, as depicted schematically in FIG. 5. Starting at the lower left of FIG. 5, a wireless sensor 12 may be implanted into the area of the body where the measurement is to be taken. In an embodiment, the wireless sensor 12 can be a cardiovascular pressure sensor that may be implanted in the body using a delivery catheter 220. This operation may be performed in a catherization lab in a hospital 210. During the implant procedure, specialized calibration equipment 230 may be provided to initially calibrate the system. The calibration equipment 230 may download calibration data, specific to the wireless sensor 12 and the reader device 10 from a remotely located database 240. Further, the calibration equipment 230 may take a reference reading during the implantation from a trusted device, such as an invasive measurement system. The calibration equipment 230 may compare the reference measurement and the wireless sensor 12 and the reader device 10 measurement to derive calibration coefficients specific to that system and patient. It may store these coefficients or upload them to the remote database 240 for use in future readings. After implantation, the patient and the associated reader device 10 may be sent to the patient's home 250, where daily readings may take place. The reader device 10 and its docking station 110 (FIG. 4) may be sent home with the implanted patient. Each day, the patient may use reader device 10 to interrogate the wireless sensor 12.

The reader device 10 may receive signals from the wireless sensor 12 in the form of raw data. The raw data may be communicated to a hub device 260, which may act as a gateway to the internet or the system network. The hub 260 may include an application 270 that processes or re-formats the raw data and further communicates it through the network. The application 270 may be a software application resident on the hub 260 and configured to perform further functions such as storage, processing, or validating the raw data. Hub 260 may be part of the docking station 110 or the reader device 10. The hub 260 may connect to the reader device 10 wirelessly or by hardwire. The hub 260 may process the raw data to be communicated to the database 240. In another embodiment, the database 240 may include a processing engine that processes the raw data for further communicating and providing useful output data. In an exemplary embodiment, the raw data may be in the form of frequency, and the processed data in the form of pressure. The database and processor 240 may use factory calibration data communicated from a factory 280 that fabricates the wireless sensor 12 and reader device 10, as well as in-situ calibration data communicated from calibration equipment 230. The application 270 may communicate software or firmware upgrades to the reader 10, change reader settings, or query the reader for status and diagnostic information. In addition to data from reader 10 readings from sensor 12, application 270 may process, store, format, or upload results of self-test data from the reader 10. The self-test data may be derived from methods and devices as described in commonly owned application Ser. No. 14/842,973 which is incorporated by reference in its entirety. Note that the database and processor 240 depicted in FIG. 5 may be an embodiment of the more general remote data gathering system 18 of FIG. 1.

The database and processor 240 may include an algorithm or logic that carries out one or more of the following functions for processing the raw data: filtering; averaging; removing bad data points according to preset criteria; conversion to final output using calibration data; authentication; validation; sanity checking; association with a known hub 260; compression/decompression; conditioning based on historical data (learning algorithms), and associating the data with a given patient. Besides sensed data, the reader device 10 and hub 260 may communicate other information such as hardware and software configuration and identification data, reader device diagnostics (temperatures, battery life, battery status, etc.), patient position (based on a tilt sensor on the reader device), ambient pressure, software alerts, and usage or event logs. The database 240 may store this data and make it available to the factory 280. The database 240 may store the raw data as well as the processed data to allow other processing to be performed on the raw data in the future.

The database 240 may communicate the raw data or the processed data to an electronic health record (EHR) database 290. The EHR database 290 may interface with a clinic 295. The interface to clinic 295 may store the processed data, or may display it graphically or in some other form. It may provide a search capability to users at the clinic 295. Users at clinic 295 may use the raw data or processed data to guide therapy for patients implanted with the wireless sensor 10.

Further, the reader device 10 may include an electrocardiogram (ECG, also called EKG). The ECG may be a touch ECG and may allow the reader device 10 to provide measured parameter data such as PA pressure as well as electrical cardiac data to the remote data interface 17. Notably, the PA pressure data and any ECG data may be analyzed by the remote data interface 17 over a period of time. Further, this data may be used for hemodynamic analysis. In particular, hemodynamic data representing pulmonary artery pressure waveforms or ECG waveforms, or both, over a time interval may be analyzed through mathematical filters/algorithms to extract useful clinical parameters. The ECG device may be a single-lead, double-lead, up through 12-lead type. The ECG leads may be stick-on wired leads that plug into the reader device 10, wireless leads, or electrodes built into the housing 120 of the reader device 10 that the patient will contact when holding the reader device 10. The ECG device may record data simultaneously with the parameters recorded by the reader device 10.

Figure 6:
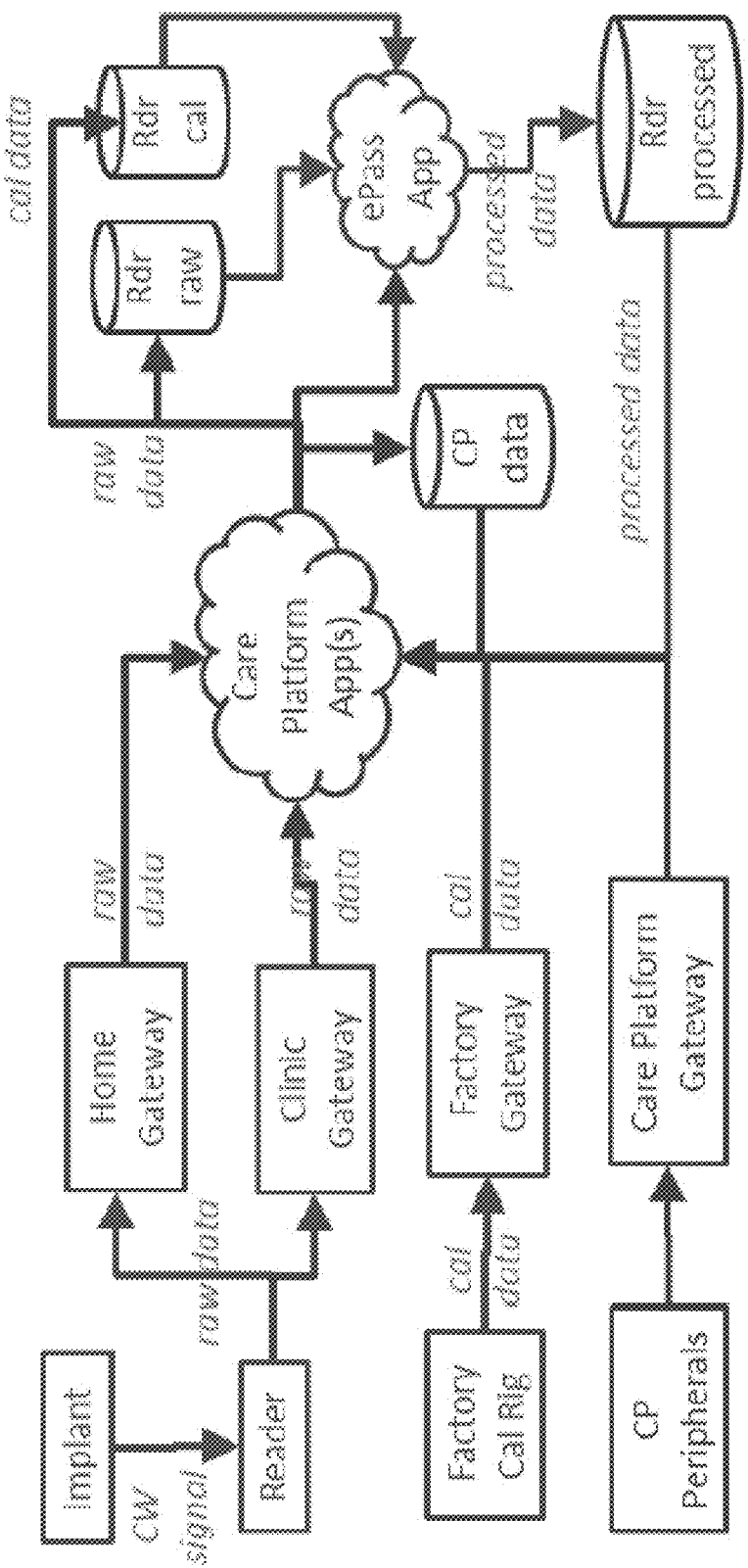
FIG. 6 illustrates embodiments of a system block diagram showing various data flows for the reader device within a sensing system.

As indicated above, the reader device 10 may communicate with a remote data interface 17. This communication pairing may be considered an internet gateway pairing that allows for secure transfer of data. There may be a plurality of different approved gateway pairings such as a home gateway, clinic gateway, factory gateway, and care platform gateway wherein each gateway pairing may be established for various communicating process steps for the flow of data. (See FIG. 6). The term "gateway" describes a device that may allow the data transferred to it to be uploaded to the internet. In the present reader embodiment, a gateway may be any device that has Bluetooth (to talk to reader) and an internet connection (Wi-Fi, cable, cellular, etc.). A gateway may be a laptop, desktop, tablet, smart phone, or custom device. The gateway—home, clinic, factory, and care platform—may be devices like these that are used in the different settings. They may differentiated by where and how they are used. So one could be a tablet and another a desktop, or they could all be smart phones, etc. The hub 260 and calibration equipment 230 may also be gateways.

The gateway pairings may be accomplished wirelessly through secure transmission such as with various wireless communication systems for example: Bluetooth, cellular, ZigBee, or Wi-Fi. In one embodiment, the remote data interface 17 may be part of the docking station 110 and the communication pairing between the docking station 110 and the reader device 10 may be configured to provide the approved gateway pairing when certain parameters are established. For example, these parameters may include when the docking station 110 and reader device 10 are located indoors, when the docking station 110 and the reader device 10 are within line-of-sight with one another, or when the docking station 110 and reader device 10 are within a specified distance from one another such as within 10 m (32.8 ft) or more particularly within 8 m (26.25 ft), within 5 m (16.4 ft) or within 3 m (9.84 ft). Additionally, the approved gateway pairings may be established when the reader device 10 is placed within the port 112 of the docking station 110. Notably, the reader device 10 may be adapted to take and store readings from the sensor 12 without an approved gateway pairing or other communication pairing having been established with the docking station 110 or the remote data interface 17. In this instance, the reader device 10 may establish the communication pairing at a later time to communicate the readings to the data interface 17. Notably, the establishment of the approved gateway pairing between the reader device 10 and the docking station 110 or the reader device 10 and the remote data interface 17 may be accompanied by audible or visual cues provided to indicate the pairing status to the user.

Other devices may be combined with the reader 10 for taking and processing different measurements. In one embodiment, a fingertip pulse oximeter may be added to the reader 10, allowing the user to record blood oxygen saturation along with the parameter measured by the wireless sensor 12. In a further embodiment, the reader 10 incorporates a connection to an arterial noninvasive blood pressure cuff. In an embodiment, these other devices may be combined with the reader 10 to take simultaneous measurements.

As indicated above, the reader device 10 may communicate with a remote data interface 17. In an embodiment, data interface 17 is a gateway device, located in the home of a patient with an implanted sensor 12, along with the patient's reader 10. The data interface 17 may be an off-the-shelf internet gateway device, such as a computer, laptop, tablet, or smart phone. The data interface 17 may have a custom app that accepts data from the reader 10 and uploads it to the internet using a WLAN, Ethernet, the cellular network, or other communication protocols. The data interface 17 may receive data from devices in the vicinity other than reader 10. The data interface 17 may upload the data to remote data system 18. The data interface 17 may be built into docking station 110. The data interface 17 may communicated over a wired connection, or wirelessly, with reader 10. In wireless embodiments, the data interface 17 may communicate with the reader 10 using Bluetooth, ZigBee, or other communication protocol. A specific reader 10 and data interface 17 may be configured to only pair with one another, to ensure security of data. The data interface 17 may store reader raw data. The data interface 17 may provide software updates from sources on the internet to the reader 10. The data interface 17 may provide calibration data to reader 10, allowing it to process its acquired data locally. The data interface 17 may perform checks on the data to ensure data integrity and may also encrypt data for privacy.

In one embodiment, the reader device 10 may be placed in various modes to carry out its functions and assist the user in its operation. Further, the reader device 10 may be configured to undergo various process steps to sample readings from the sensor 12 and communicate these sampled readings in an efficient way. The reader device 10 may be programmed to include an algorithm that automatically allows the reader to switch between the various modes when a particular criterion has been satisfied. The criterion may be in response to user inputs, or determined by programmable threshold values of sensed parameters.

Figure 7A:
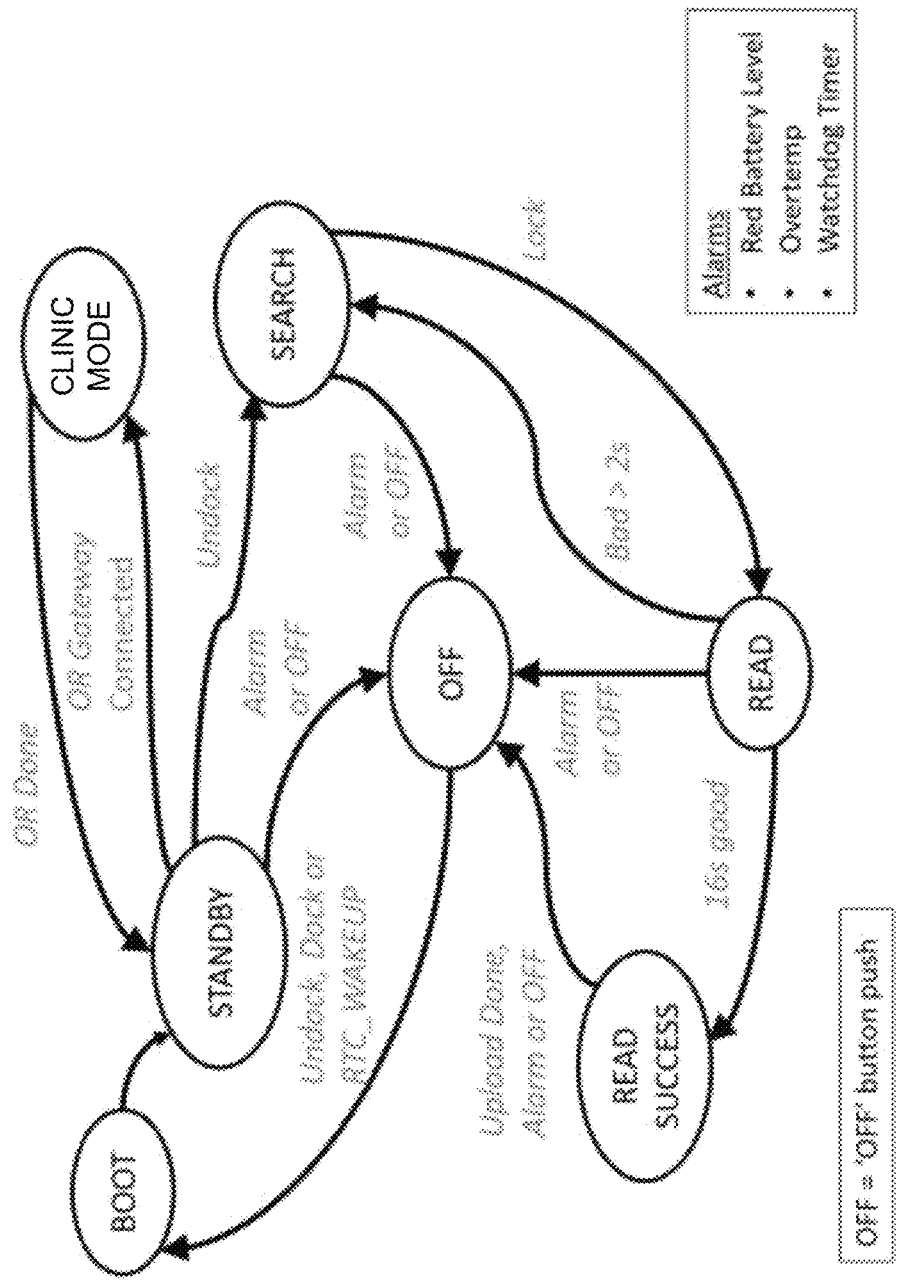
FIG. 7A illustrates an embodiment of a state diagram of various operational modes of the reader device and system.
Figure 8:
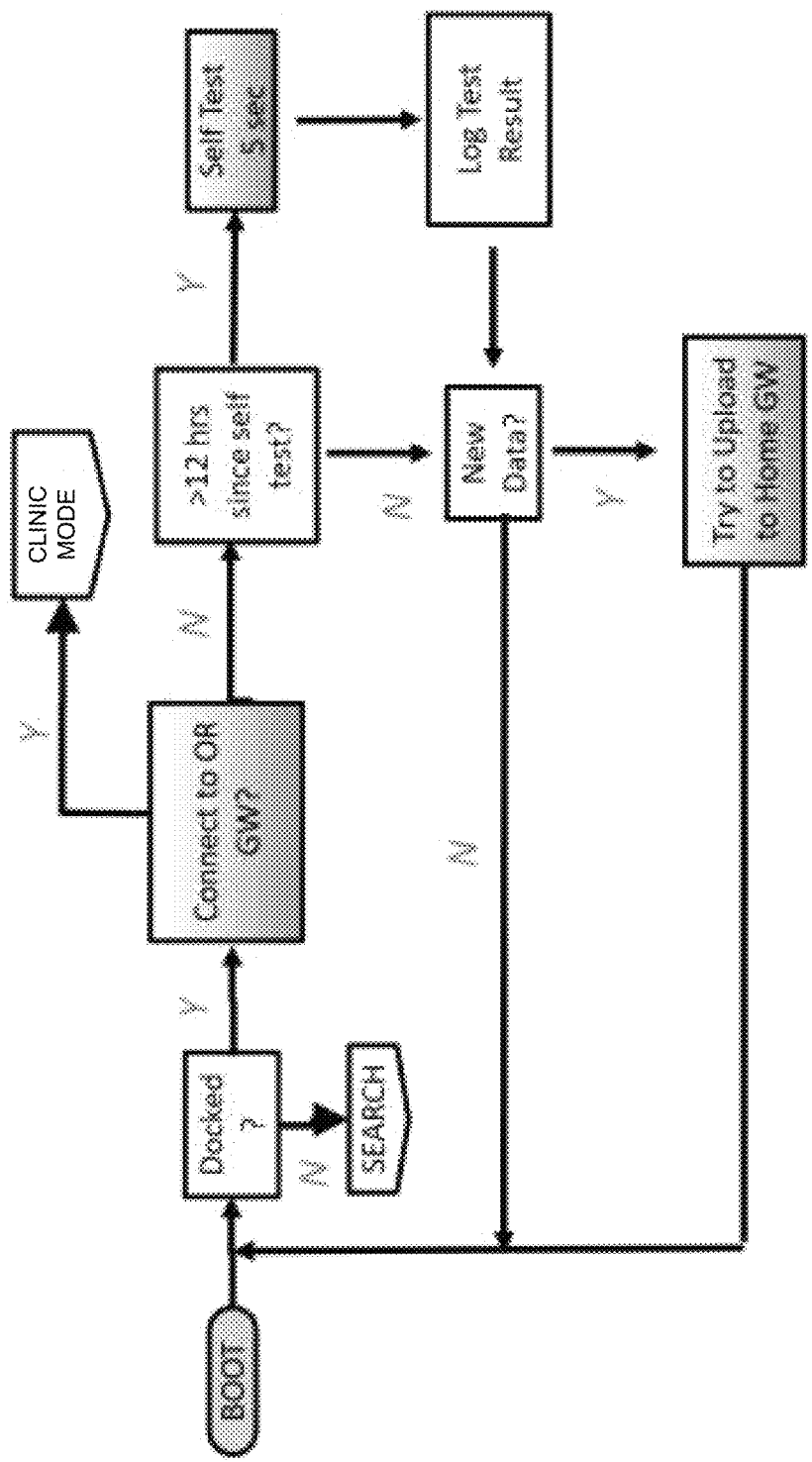
FIG. 8 illustrates a flow diagram of a standby mode of the reader device and system.

FIG. 7A is an embodiment of a state diagram that illustrates various states or modes the reader device 10 may operate. The change from one mode to the other may be automatic and otherwise require minimal input by the user to toggle between modes. The chart identifies that the reader device 10 may toggle between an off mode, a boot mode, a standby mode, a clinic mode, a search mode, a read mode, and a read success mode. In the off mode, the reader device 10 may be shut down. Here the reader device 10 may be docked or positioned within the port 112 of the docking station 110. As the reader device 10 is removed from the port 112, the reader may be placed in the boot or wake up mode. Once booted up, the reader device 10 may then be placed in the standby mode and may go into search mode if the reader device 10 is removed from the port 112 ("undocked") by a user (See FIG. 8). The reader device 10 may automatically determine whether it is docked or not. If, from Standby mode, the reader device 10 connects to a clinic-based gateway, the reader device 10 may be placed in clinic mode and otherwise be ready to connect with an approved gateway pairing as described. Further, from standby mode, the reader device 10 may execute a self-test. The reader may execute a self test if the reader device 10 has been docked or otherwise has undergone no self test within a duration of time, such as for about 12 hours (this duration may be programmable and adjustable). The self test mode is described in commonly owned U.S. patent application Ser. No. 14/842,973 which is incorporated by reference in its entirety. Further, from standby mode, the reader device 10 may attempt to connect with a gateway to upload new data, old data, or diagnostic or logistical data, including event logs, warnings and errors, temperature, battery voltage, or any data generated by the self-test. Any failures to connect or attempts at pairing may also be logged and locally stored by the reader device 10, and the logs may be uploaded to the gateway. Notably, if the reader device 10 becomes undocked during the clinic mode or self-test mode, the reader device may abort the current operation and proceed to search mode. Note that in FIG. 7A, the abbreviation "OR" stands for operating room and "RTC" stands for real time clock.

Figure 7B:
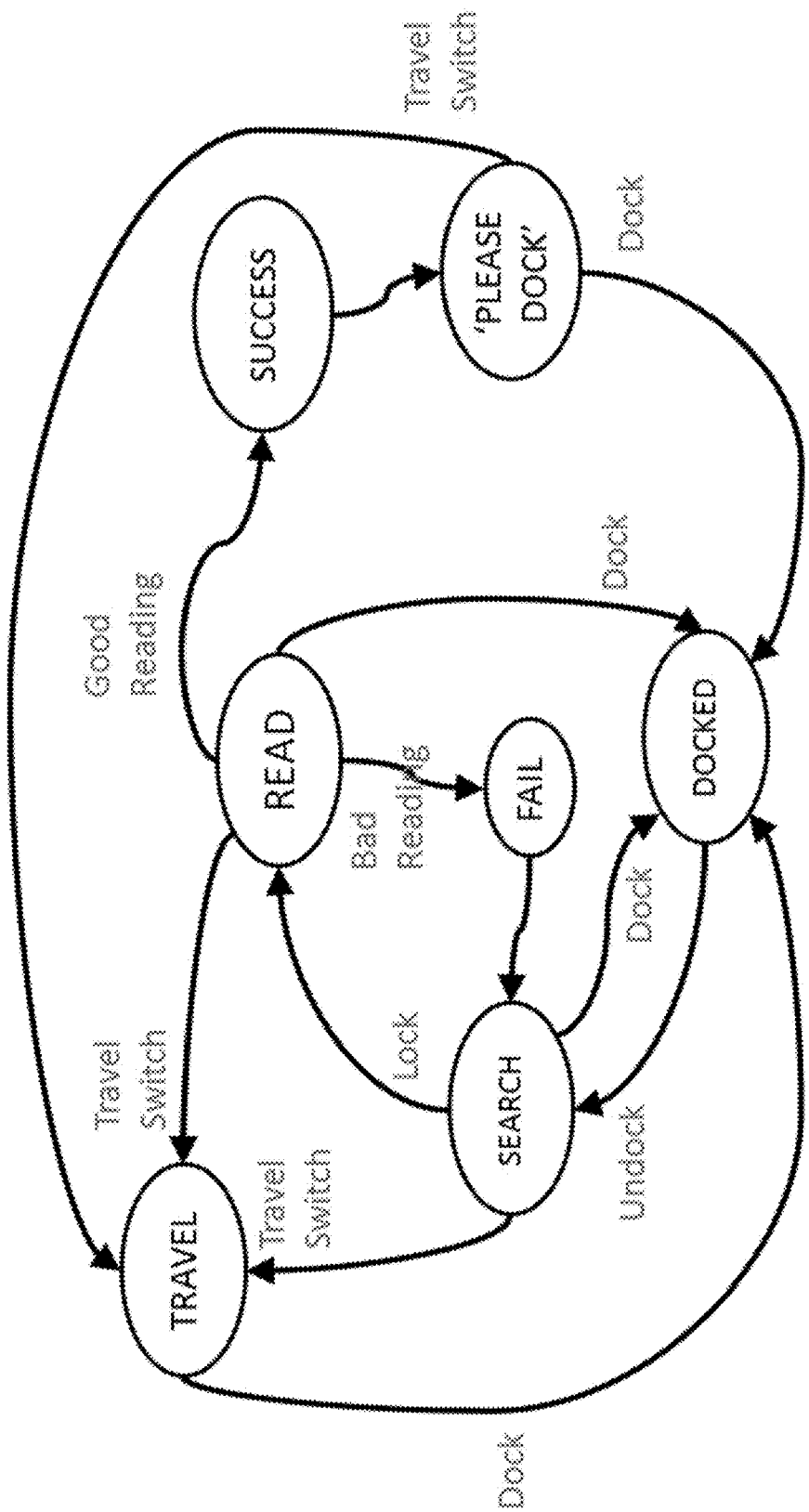
FIG. 7B illustrates another embodiment of a state diagram of various operational modes of the reader device and system.

FIG. 7B illustrates another embodiment of a state diagram showing various modes of operation. The labeled arrows indicate events that occur to move from one state to another. The change from one mode to the other may require minimal or no user input. In many embodiments, particularly those in which the user is a medical patient, it is advantageous to keep user operation simple. In this embodiment, the diagram indicates that the reader device 10 may toggle between a "docked" mode, a "search" mode, a "read" mode, a "success" mode, a "fail" mode, a "please dock" mode, and a "travel" mode. In the docked mode, the reader device 10 may be shut down or dark. Notably, the reader device 10 may automatically determine whether it is docked or not. Here the reader device 10 may be docked or positioned within the port 112 of the docking station 110. The reader and docking station may operate to recharge the reader's batteries. Further, from the docked mode, the reader device 10 may execute a self-test as described above. Further, from docked mode, the reader device 10 may attempt to connect with a network gateway device to upload new data, old data, or diagnostic or logistical data, including event logs, warnings and errors, reader ID, timestamped raw frequency data captured from the sensor 12, ambient pressure reading, transmit frequency selected, battery charge level or voltage, average signal strength for the reading, internal temperatures, boundary scan or watchdog timer status, and optional other diagnostic or logistical data or any data generated by the self-test. The reader 10 may mark all past data as "uploaded" or "not uploaded" and only upload data that has not previously been uploaded. Communication with the network or gateway may also include reader software or firmware updates, changes to reader settings, real-time clock synchronization, or other data downloads. Any failures to connect or attempts at pairing may also be logged and locally stored by the reader device 10 and may be uploaded to the gateway. As the reader device 10 is removed from the port 112, the reader may wake up. Once booted up, the reader device 10 may then go into search mode if the reader device 10 is removed from the port 112 ("undocked") by a user. Notably, if the reader device 10 becomes undocked during gateway communications or self-test mode, the reader device may abort the current operation and proceed to search mode.

Various conditions may also occur at any point in the state machine, which may cause the reader 10 to toggle modes, such as powering off. For example, the reader 10 may execute a safe shutdown in the event of low battery, internal over-temperature of critical circuits, watchdog timer failure, undefined logic state, or other off-nominal state where device safety and performance would require a shutdown. In the case of an automatic shutdown, the reader 10 may restart when the reader is in its dock and the off-nominal condition causing the shutdown no longer exists.

Figure 9:
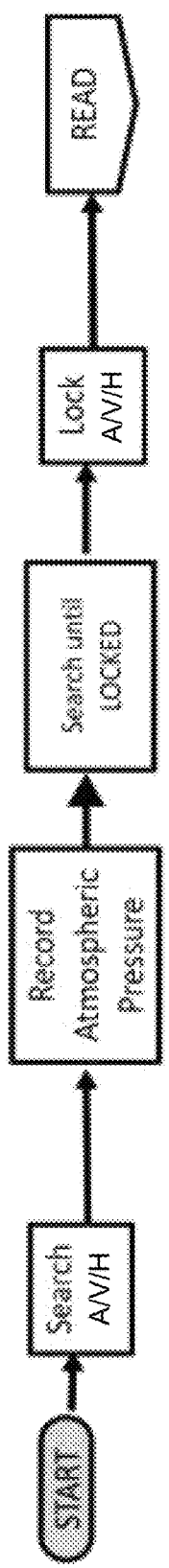
FIG. 9 illustrates a flow diagram of a search mode of the reader device and system.

FIG. 9 further illustrates the reader device 10 as it is placed in search mode. Upon entering search mode, the reader device 10 may undergo various processes including initiating an audio, visual, or haptic (A/V/H) signal indicating the reader is in search mode, recording atmospheric pressure, searching until lock conditions are met, and initiating an A/V/H signal that indicates a lock with the sensor 12 has been accomplished. In search mode, the patient may move the reader device 10 towards a location proximate to the implanted sensor 12. Here, the reader device 10 attempts to establish the proper distance $D_1$ (FIG. 2) that may be acceptable for taking readings from the sensor 12. The reader device 10 may include a lock circuitry 22 (FIG. 2) to detect signal strength that emanates from the sensor 12. In particular, the lock circuitry 22 may detect the signal strength of the response signal 16 as the reader device 10 is positioned or moved in position adjacent to the location of the sensor 12 such as within the body of the patient. Note that although FIG. 2 shows RF link distance $D_1$ in a direction normal to the centerlines of reader 12 and sensor 10, the reader 10 and Sensor 12 may also be offset laterally from one another, may be positioned at any angle with respect to one another, and generally may assume any position relative to one another, influencing the magnitude and direction of $D_1$. The lock circuitry 22 may be configured to measure an amplitude of the response signal 16. Further, the lock circuitry 22 may be configured to compare the measured amplitude of the response frequency signal 16 relative to a threshold measurement. The threshold measurement may be known or otherwise programed within the lock circuitry 22. Additionally, the threshold measurement may be based on (i) a threshold calibration reading taken at a predetermined time under controlled conditions, (ii) an instruction directly input from the user at the docking station, or (iii) a signal from an outside source. Notably, the lock circuitry 22 may be located within the reader device 10, docking station 110, or remotely located and communicated through an outside source such as a network. The lock circuitry 22 may be a processor, programmable logic controller, or other arrangement of electrical components arranged to establish the measurements and comparisons as described.

The lock circuitry 22 may also be able to communicate with the external or remote data interface 17 to identify whether the reader device 10 is within sufficient proximity to the sensor 12 to establish proper communication. This sufficient proximity or "lock" on the sensor 12 may be identified by the lock circuitry 22 and communicated to the data interface 17 such that an output signal may be generated. The output signal may be in the form of an audible, visual, or haptic signal illustrated on the display 21 or provided by the reader device 10 to notify the user that the location of the reader device 10 is in sufficient proximity to the sensor 12 for establishing communication as it is implanted within the patient. Sufficient proximity may exist when the reader device 10 is aligned with the sensor 12 along a common axis 50 and within an RF link distance $D_1$ (See FIG. 2). Notably, the reader device 10 may be configured to accurately measure the response signal 16 of the sensor 12 when the reader device 10 and sensor 12 have a link distance $D_1$ of about 5 cm (1.97 in) to about 30 cm (11.8 in) and more particularly between 9 cm (3.54 in) to about 15 cm (5.91 in). Notably, a portion of link distance $D_1$ may be through a patient's body as well as clothing on the patient. The A/V/H signal may comprise a set of tones, vibrations, or flashing lights, which increase in frequency as the reader 10 moves closer to alignment with the implant 12, and decreases in frequency as the reader moves further away from alignment with the implant 12. The A/V/H signal may also comprise spoken voice prompts.

Figure 10:
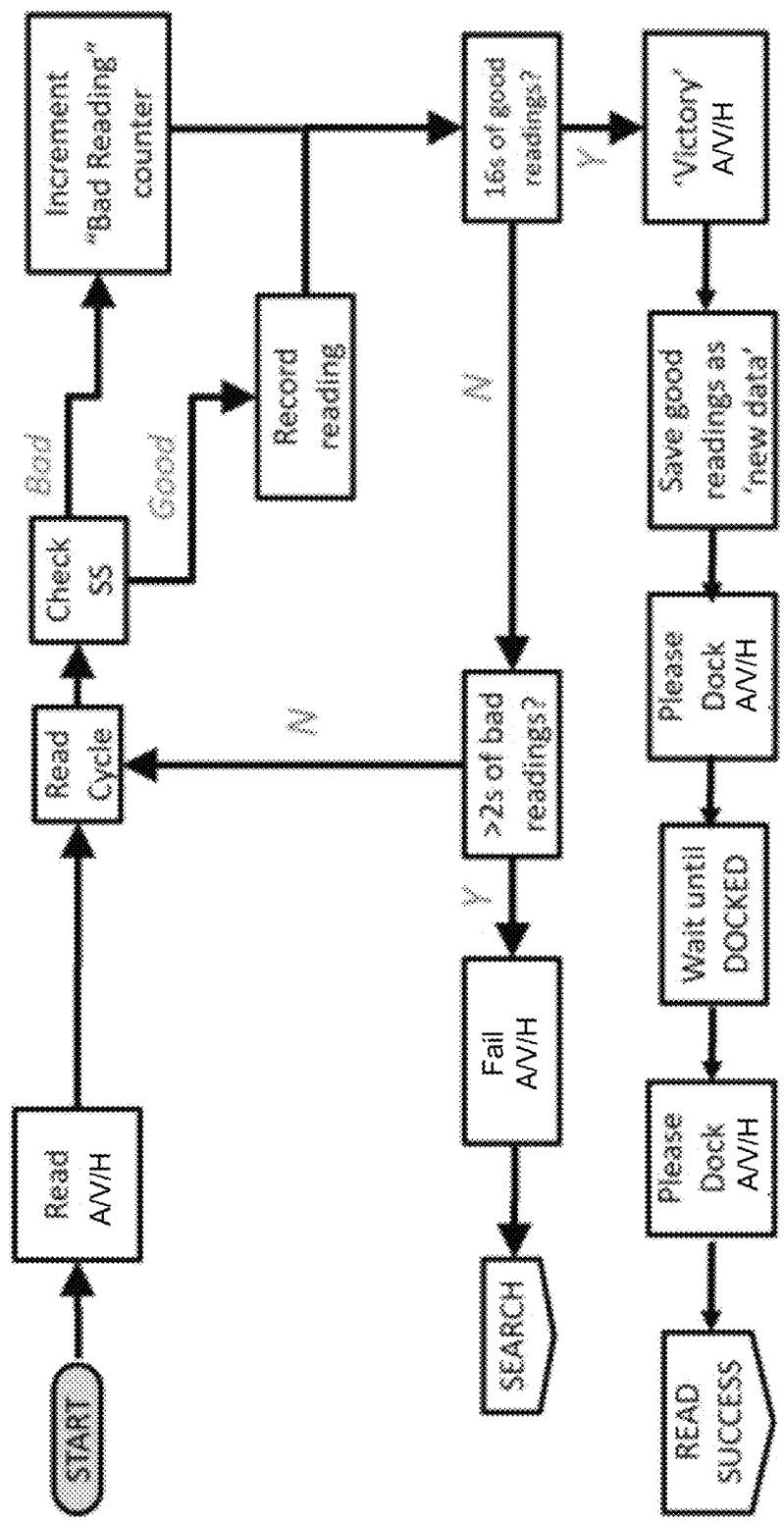
FIG. 10 illustrates a flow diagram of a read mode of the reader device and system.

Referring now to FIGS. 7B and 10, the reader device 10 may produce a plurality of stimulus signals 14 in search mode. Once the reader device 10 has identified at least one response signal 16 or a sufficient number of response signals 16 that includes an amplitude over a threshold value, the reader device 10 may then be considered locked and may enter the read mode to read and sample the responding response signals 16 from the sensor 12.

Once the reader device 10 and the sensor 12 have been identified to be locked, the reader device 10 may enter the read mode. The reader device 10 may provide an A/V/H signal to the user to indicate a lock on the sensor 12. The A/V/H signal may instruct the user to hold the reader device 10 in a steady position for an amount of time sufficient to complete a number of read cycles; each read cycle may comprise transmission of a stimulus pulse, and reception of at least one response signal from the sensor. The number of read cycles may be determined by: (i) a predetermined time; (ii) a predetermined number of cycles; (iii) a predetermined number of cycles wherein the reading obtained is deemed valid according to a predetermined criterion; or (iv) detection of an event or events, such as a set number of cardiac cycles or respiration cycles. As illustrated by FIG. 10, in read mode the reader device 10 may be configured to read and record the response signals 16 generated by the sensor 12. Further, the lock circuitry 22 may also identify whether a given reading from the sensor 12 is valid or not valid. Validity of a reading may be based on a predetermined parametric threshold, such as a response signal strength being above a certain amplitude. The reading device 10 may keep a running count of valid and invalid data points (a "data point" here is the result of one read cycle). If the number of invalid data points exceeds a predetermined amount, either cumulatively or continuously, the reading device 10 may issue an A/V/H signal indicating a "failed read session" designated "FAIL" in FIG. 7B. In this case the reading device 10 may re-enter search mode, allowing the user to attempt to initiate a new lock on sensor 12 and to try again. Additionally, if the number of valid data points exceeds a preset threshold, the reading device 10 may issue an A/V/H signal indicating a "successful read session." The reading device 10 may store valid data points in memory and may reject invalid ones. The reading device 10 may timestamp each individual data point. The reading device 10 may use an A/V/H signal to instruct the user to re-dock the reading device 10 after a successful read session. The reading device 10 may log valid and invalid reading attempts, as well as successful and failed read sessions for diagnostic purposes. The lock circuitry 22 may generate a signal to indicate that an additional reading may be required or that the reading received is sufficient to extrapolate the measurement of the desired parameter. In an exemplary embodiment, the reader device 10 may declare a "failed read session" when more than 2000 cumulative (not necessarily consecutive) invalid data points have been counted, and may declare a "successful read session" when more than 16000 valid data points have been counted. However, this disclosure is not limited to these amounts for declaring failed or successful read sessions.

Once a successful reading has been completed, the reader 10 may enter "please dock" mode as illustrated by FIG. 7B. Here, an A/V/H signal may cue the user to "please dock." The reader 10 may continue to issue the "please dock" A/V/H signal until the user docks the reader engaged with the docking station 110. Alternatively, the reader's state machine may not feature a "please dock" mode. In such an embodiment, the reader may repeatedly issue the "success" A/V/H signal, or may remain silent and dark.

Figure 11:
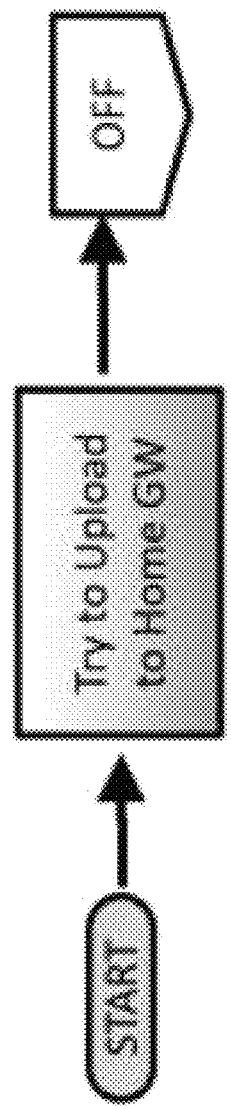
FIG. 11 illustrates a flow diagram of a read success mode of the reader device and system.

During read success mode as illustrated by FIG. 11, the sampled signals may be communicated or otherwise uploaded to the remote data interface 17 or docking station 110. The reader device 10 may communicate the new data to a gateway. If the reader device 10 is docked, it may return to standby mode, and upload data to the remote data interface 17 from that mode. If in standby mode or read success mode, the reader device 10 may then be placed in off mode if not engaged in uploading data or performing self-test. Each reading that is uploaded to the gateway or stored in the reader device 10 may include the following information: a reader ID, timestamped raw frequency data captured from the sensor 12, ambient pressure reading, transmit frequency selected, battery charge level, average signal strength for the reading, internal temperatures, boundary scan or watchdog timer status, and optional other diagnostic or logistical data.

The reader device 10 or the docking station 110 may prompt A/V/H signals that identify the status of the reader device 10 and to prompt the user to dock the reader device 10 when not in use, so that battery of the reader device 10 may be recharged and also to prevent misplacement of or inadvertent damage to reader device 10. Notably, the A/V/H signal for "search mode" may be a beep, buzz, vibration, or voice prompt that is slightly unpleasant or annoying, motivating the user to either obtain a lock on a sensor (and trigger read mode) or re-dock the reader device 10 (and trigger standby mode)—both read and standby modes would feature a more pleasant A/V/H signal, or no A/V/H signal. Motivating the user to get out of search mode as quickly as possible will discourage behaviors such as leaving the reader device 10 undocked on a tabletop, placing the reader device 10 in a pocket, or carrying it to locations away from the docking station. Further, the docking station may provide a pushbutton or other means to cause an undocked reader device 10 to issue an A/V/H signal, allowing the user to find the Reader if it has been misplaced.

To ensure simple operation by a wide variety of users, user actions may be limited to undocking, searching, reading, and re-docking. All other system functions, including data upload, self-test, pairing and communicating with external devices, etc., may be done in non-real time and may be invisible to the user.

For embodiments in which the reader device 10 is portable, a user may take the reader device and docking station along when traveling, so as not to miss daily readings. The reader device 10 may also feature a "travel" switch for situations wherein the user wants to travel to a different location with the reader device 10. The "travel" switch would allow the user to manually place the reader device 10 in travel mode so that the continuous beeping while undocked and in Search mode would not become a nuisance. Once at the new location, the reader device 10 could be re-activated by docking to a powered dock, which would boot up the reader device 10 and place it again in docked mode per the normal state machine.

Notably, the display 21 may provide A/V/H signals to identify the mode status of the reader device 10, i.e. when the reader device 10 is in "search" mode, "read" mode, standby mode, clinic mode, docked mode, travel mode, off mode, whether an approved gateway pairing is established, or if the reader device 10 is charging. Alternatively, such a display may be built into the reader 10, the hub 260, or the docking station 110. The reader device 10 may include a tilt sensor 28 such as an accelerometer or other type of position sensor to allow the reader device 10 to identify if the patient is sitting/standing, or laying down during the reading (See FIG. 2). The tilt sensor 28 may measure a tilt of the reader device 10 along one or more axes normal to the reader surfaces 122 with respect to earth's gravity. The patient's position may affect the sensed parameter, e.g. pulmonary artery pressure (and other pressures inside the body), due to shifting of one's body mass. For embodiments where the tilt sensor 28 is an accelerometer, the accelerometer may also provide an indication that a patient is walking or moving in a vehicle (car or wheelchair) while taking a reading, or whether the patient's hand is shaking while holding the reader device 10. Further, it may be desirable for the patient to be in the same position (upright versus supine) for each reading, to ensure reading consistency. To ensure this, the reader device 10 may issue an A/V/H signal prompting the patient to assume to correct position, if the tilt sensor 28 detects an incorrect position. The reader device 10 may further not take a reading until the position has been corrected.

The tilt sensor 28 may also be used as a manual switch. In one embodiment, the tilt sensor 28 may be used to place the reader 10 into travel mode. The user may tilt the reader device 10 to a given position, for example with the reading surface 122 pointed upwards with respect to gravity, and hold it there for several seconds, in order to place the reader device 10 in travel mode, as schematized in FIG. 7B.

Further, the portability feature of the reader device 10 may be enhanced by including location finding capability, which may be of interest to diagnosticians observing reader data. In an embodiment, the reader device 10 may include circuitry allowing it to use the Global Positioning System (GPS) to determine its location during a given reading, and upload this information. In another embodiment, the docking station 110 or the hub 260 may contain the location circuitry. In other embodiments, the reader device 10 or its docking station 110 may obtain location information from a third device, such as a paired internet gateway. Location information may be useful in determining local time, or weather conditions that may affect the sensed parameter, for example barometric pressure.

The embodiments of the disclosure have been described above and, obviously, modifications and alternations will occur to others upon reading and understanding this specification. The claims as follows are intended to include all modifications and alterations insofar as they are within the scope of the claims or the equivalent thereof.

Having thus described the invention, We claim:

1. A system for wirelessly sensing a parameter from a remote location, comprising:
    a handheld reader device configured to communicate with a wireless sensor;
    wherein said handheld reader device includes a plurality of modes to establish communication with said wireless sensor, said modes comprising:
        a docked mode wherein said handheld reader device is not in use;
        a search mode wherein said handheld reader device attempts to establish the proper distance acceptable for taking readings from the wireless sensor, wherein when said handheld reader device is in said search mode, said handheld reader device is configured to receive at least one response signal from said wireless sensor and compare a characteristic of said at least one response signal to a predetermined threshold value, wherein said comparison of said characteristic of the at least one response signal to said predetermined threshold value is used to determine to provide a feedback to a user of said handheld reader device; and
        a read mode wherein said handheld reader device reads and samples response signals from the wireless sensor.

2. The system of claim 1, wherein said wireless sensor is configured to change its resonant frequency in proportion to at least one sensed parameter.

3. The system of claim 1, wherein said wireless sensor is a passive sensor.

4. The system of claim 1, further comprising a remote data interface to communicate with said reader device.

5. The system of claim 1 further comprising a docking station configured to receive said handheld reader device and to electrically communicate with said handheld reader device.

6. The system of claim 5, wherein said reader device includes a battery.

7. The system of claim 6, wherein said docking station is configured to recharge said battery of the reader device.

8. The system of claim 5, wherein said docking station includes a remote data interface that is configured to accept raw frequency data and format it for communication with a remote device.

9. The system of claim 5, wherein said docking station is configured to provide a data link function and a data storage function.

10. The system of claim 1, wherein said wireless sensor is implanted within a human patient.

11. The system of claim 1, wherein said comparison of said signals to said predetermined threshold value is made by a device external to said reader device.

12. The system of claim 1, wherein said comparison of said signals to said predetermined threshold value are displayed on a screen.

13. The system of claim 1, wherein said feedback comprises audible, visual, or haptic signals.

14. The system of claim 1, wherein said feedback is configured to guide said user to locate said handheld reader device in a position aligned relative to said sensor that enables wireless communication.

15. The system of claim 1, wherein said feedback is configured to inform said user that alignment with said sensor has been achieved establishing a locked condition between said reader device and said wireless sensor and causing said handheld reader device to enter said read mode.

16. The system of claim 1, wherein said handheld reader device processes said strength of said signals to determine that a sufficient number of acceptable reading samples are obtained during read mode.

17. The system of claim 16, wherein said handheld reader device is configured to determine that a reading attempt of the wireless sensor is successful or unsuccessful and to provide an audible, visual, or haptic signal to said user identifying a passed or a failed reading attempt.

18. A wireless sensor reader device comprising:
a transmit circuit configured to generate an excitation pulse to cause a wireless sensor to energize and emit a response signal; an antenna configured to transmit said excitation pulse and receive said response signal; a lock circuit for evaluating whether said wireless sensor is in sufficient proximity to said reader device to take readings from said wireless sensor; wherein said reader device is handheld;
wherein said reader device uploads said response signal data to a remote database and processor; wherein said response signal data is uploaded as raw data and processed according to an algorithm to produce processed data.

19. The wireless sensor reader device of claim 18, wherein said reader device further comprising a fingerprint sensor.

20. The wireless sensor reader device of claim 18, wherein said reader device is configured to ensure that designated users operate said reader device.

21. The wireless sensor reader device of claim 19, wherein said reader device is configured to associate data from said fingerprint sensor with the data captured during a reading event.

22. The wireless sensor reader device of claim 18, wherein said reader device further comprising a circuit for measuring electrocardiogram data.

23. The wireless sensor reader device of claim 22, wherein said circuit comprises remote electrodes that connect to said reader device.

24. The wireless sensor reader device of claim 23, wherein said electrocardiogram circuit comprises electrodes that are built into the surface of said reader device.

25. The wireless sensor reader device of claim 22, wherein said circuit for measuring electrocardiogram data is selected from among the following types of electrocardiogram measurement: one lead, two leads, four leads, eight leads, and twelve leads.

26. The wireless sensor reader device of claim 22, wherein said reader device measures and records data from said wireless sensor and said electrocardiogram simultaneously.

27. The wireless sensor reader device of claim 18, further comprising a tilt sensor.

28. The wireless sensor reader device of claim 27, wherein said tilt sensor is an accelerometer.

29. The wireless sensor reader device of claim 27, wherein said tilt sensor is configured to record an orientation of said reader device with respect to gravity.

30. The wireless sensor reader device of claim 28, wherein said accelerometer is configured to record motion of the reader device during a reading mode.

31. The wireless sensor reader device of claim 18, further comprising a means for authenticating a user by recording speech from said user, and associating said speech record with data derived from a given reading.

32. The wireless sensor reader device of claim 22, wherein said electrocardiogram data is combined with a parametric data from said wireless sensor to enable hemodynamic analysis.

33. The wireless sensor reader device of claim 18, wherein said reader device includes circuitry for determining its geographic location.

34. The system of claim 5, wherein said handheld reader device enters said search mode automatically upon being removed from said docking station.

35. The system of claim 1, wherein said handheld reader device is configured to enter a travel mode, wherein said travel mode places said handheld reader device in a state conducive to transport to a new location such that said handheld reader device is configured to inhibit at least one audible, visual, or haptic signal.

36. The system of claim 35, wherein a user may place said handheld reader device into said travel mode by a switch, said switch comprises at least one of: a mechanical switch, a capacitive switch, a tactile switch, a voice-activated switch, a toggle switch, a momentary switch, an accelerometer, a tilt sensor, a spoken command, and a fingerprint sensor.

37. The system of claim 5, wherein said handheld reader device and said docking station are configured to execute a self-test while said reader device is placed in said docking station.

38. The wireless sensor reader device of claim 18, wherein said remote database and processor stores said raw data and said processed data.

39. The wireless sensor reader device of claim 38, wherein said algorithm utilizes calibration data originally obtained during the manufacture of said reader device or said wireless sensor.

40. The wireless sensor reader device of claim 18, wherein said algorithm utilizes calibration data obtained during surgical implantation of said wireless sensor into a patient.

41. The wireless sensor reader device of claim 18, wherein said algorithm utilizes historical data processed by said reader device.

42. The wireless sensor reader device of claim 41, wherein said algorithm is a learning algorithm.

43. The wireless sensor reader device of claim 18, wherein said processed data is representative of a strength of said response signal received by said wireless sensor.

44. The wireless sensor reader device of claim 43, wherein said reader device is configured to reject said response signals that fail to meet said at least one predetermined threshold.

45. The wireless sensor reader device of claim 18, wherein said algorithm utilizes data taken from a second sensor configured to measure a parameter different from the parameter measured by the first said wireless sensor.

46. The wireless sensor reader device of claim 45, wherein said second sensor is selected from among the following sensor types: barometer, accelerometer, tilt sensor, blood glucose sensor, inspiration spirometer, pulse oximeter, arterial blood pressure sensor, electrocardiogram, weight scale, or echo-cardiogram.

47. The wireless sensor reader device of claim 18, wherein said wireless sensor is implanted in a patient, and said algorithm utilizes data taken from said patient's medical record.

48. The wireless sensor reader device of claim 18, wherein wireless sensor is implanted in a patient, and said algorithm utilizes data taken from said patient's answers to health related questions.

49. The wireless sensor reader device of claim 46, wherein said second sensor is connected to said reader device.

50. The wireless sensor reader device of claim 18, wherein said algorithm is a hemodynamic algorithm.

51. The system of claim 5, wherein said reader device further enters a mode wherein at least one audio, visual, or haptic signal guides a user to place said reader device onto said docking station.

52. The system of claim 1, wherein said characteristic of said at least one response signal is the strength of said signal.

53. The system of claim 1, wherein said at least one response signal is a ring signal.

54. The system of claim 1, wherein said at least one response signal is a digital signal.

55. The device of claim 18, wherein said at least one response signal is a ring signal.

56. The device of claim 18, wherein said at least one response signal is a digital signal.

* * * * *